(12) United States Patent
Makifuchi et al.

(10) Patent No.: US 9,510,799 B2
(45) Date of Patent: Dec. 6, 2016

(54) MEDICAL IMAGING SYSTEM AND MEDICAL IMAGE PROCESSING APPARATUS

(71) Applicant: Konica Minolta, Inc., Tokyo (JP)

(72) Inventors: Chiho Makifuchi, Hino (JP); Kazuhiro Kido, Hino (JP); Junko Kiyohara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 176 days.

(21) Appl. No.: 14/406,565

(22) PCT Filed: May 1, 2013

(86) PCT No.: PCT/JP2013/062690
§ 371 (c)(1),
(2) Date: Dec. 9, 2014

(87) PCT Pub. No.: WO2013/187150
PCT Pub. Date: Dec. 19, 2013

(65) Prior Publication Data
US 2015/0131777 A1 May 14, 2015

(30) Foreign Application Priority Data

Jun. 11, 2012 (JP) .................................. 2012-131596

(51) Int. Cl.
*G01N 23/04* (2006.01)
*A61B 6/00* (2006.01)
*G06T 11/00* (2006.01)

(52) U.S. Cl.
CPC ........... *A61B 6/5217* (2013.01); *A61B 6/4291* (2013.01); *A61B 6/463* (2013.01); *A61B 6/483* (2013.01);
(Continued)

(58) Field of Classification Search
CPC ......... A61B 6/4233; A61B 6/54; A61B 6/461; A61B 6/482; A61B 6/5241; A61B 6/463
See application file for complete search history.

(56) References Cited

U.S. PATENT DOCUMENTS

2009/0316857 A1* 12/2009 David ................... A61B 6/484
378/62
2011/0243302 A1* 10/2011 Murakoshi ............. G01N 23/04
378/62

(Continued)

FOREIGN PATENT DOCUMENTS

JP          200393377 A     4/2003
JP         2005034539 A     2/2005

(Continued)

OTHER PUBLICATIONS

International Preliminary Report on Patentability and Written Opinion of the International Searching Authority corresponding to Application No. PCT/JP2013/062690; Date of Mailing: Dec. 16, 2014, with English translation.

(Continued)

*Primary Examiner* — Hoon Song
(74) *Attorney, Agent, or Firm* — Cantor Colburn LLP

(57) ABSTRACT

A medical imaging system creates three kinds of reconstructed images of a diagnosis target site in a subject through X-ray imaging of the diagnosis target site with a Talbot or Talbot-Lau imaging apparatus, the three kinds of reconstructed images being an absorption image, a differential phase image, and a small-angle scattering image. The medical imaging system includes: an input unit to receive an input of diagnosis target information for specifying the diagnosis target site, or the diagnosis target site and a disease to be diagnosed in the diagnosis target site; and a control unit to create a combined image of two kinds of reconstructed images among the three kinds of reconstructed images on the basis of the diagnosis target information input through the input unit, and to control a displaying unit to display the combined image.

13 Claims, 20 Drawing Sheets

(52) U.S. Cl.
CPC ............. *A61B 6/484* (2013.01); *A61B 6/5235* (2013.01); *G06T 11/00* (2013.01); *A61B 6/502* (2013.01); *A61B 6/505* (2013.01)

(56) References Cited

U.S. PATENT DOCUMENTS

| | | | | |
|---|---|---|---|---|
| 2012/0128126 | A1* | 5/2012 | Ishii | A61B 6/4291 378/62 |
| 2012/0140885 | A1* | 6/2012 | Iwakiri | A61B 6/06 378/62 |

FOREIGN PATENT DOCUMENTS

| | | |
|---|---|---|
| JP | 2009525084 A | 7/2009 |
| JP | 2010187774 A | 9/2010 |
| JP | 2011015848 A | 1/2011 |
| JP | 2011206239 A | 10/2011 |
| JP | 2012170618 A | 9/2012 |
| WO | 2004058070 A1 | 7/2004 |
| WO | 2011033798 A1 | 3/2011 |
| WO | 2011114845 A1 | 9/2011 |
| WO | 2012029340 A1 | 3/2012 |

OTHER PUBLICATIONS

International Search Report for International Application No. PCT/JP2013/062690, issued Jul. 30, 2013, with English translation.

Kazuhiro Kido, "X-ray Imaging Technology Using a Talbot-Lau Interferometer", Konica Minolta Technology Report, Jan. 2011, vol. 8, pp. 82-85.

Thomas Thuring et al., "Non-Linear Regularized Phase Retrieval for Unidirectional X-ray Differential Phase Contrast Radiography", Optics Express, vol. 19, No. 25, 2011, pp. 25545-25558.

Wataru Yashiro et al., "Distribution of Unresolvable anisotropic microstructures revealed in visibility-contrast images using x-ray Talbot Interferometry", Physical Review B 84, 094106 (2011).

\* cited by examiner

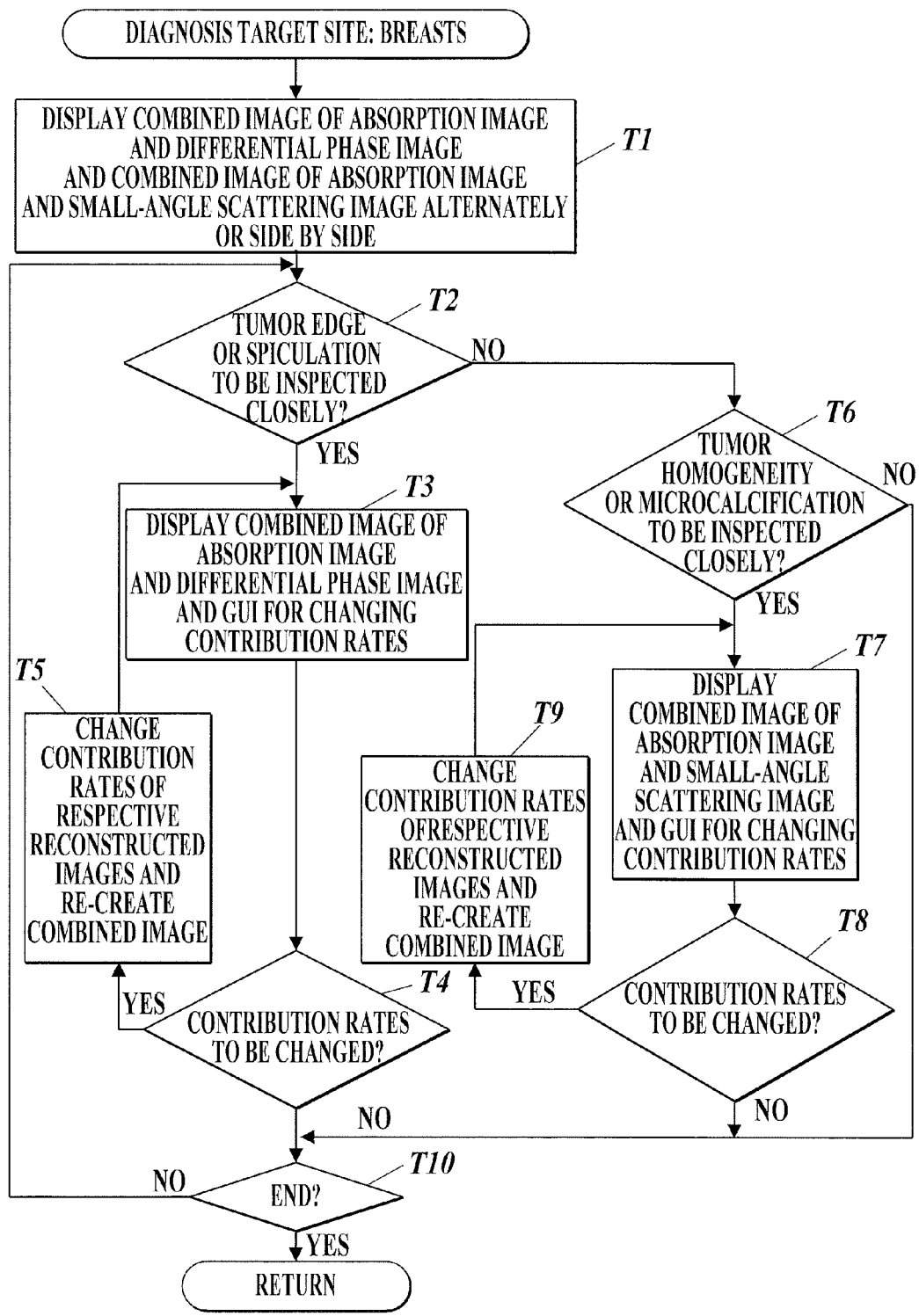

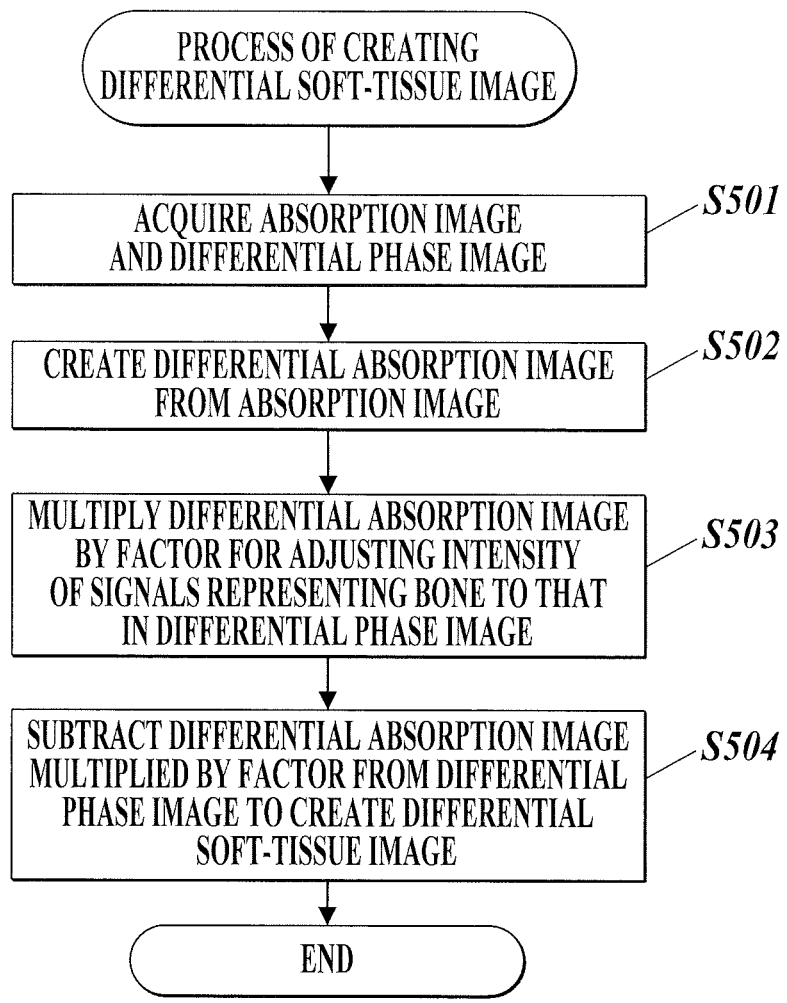

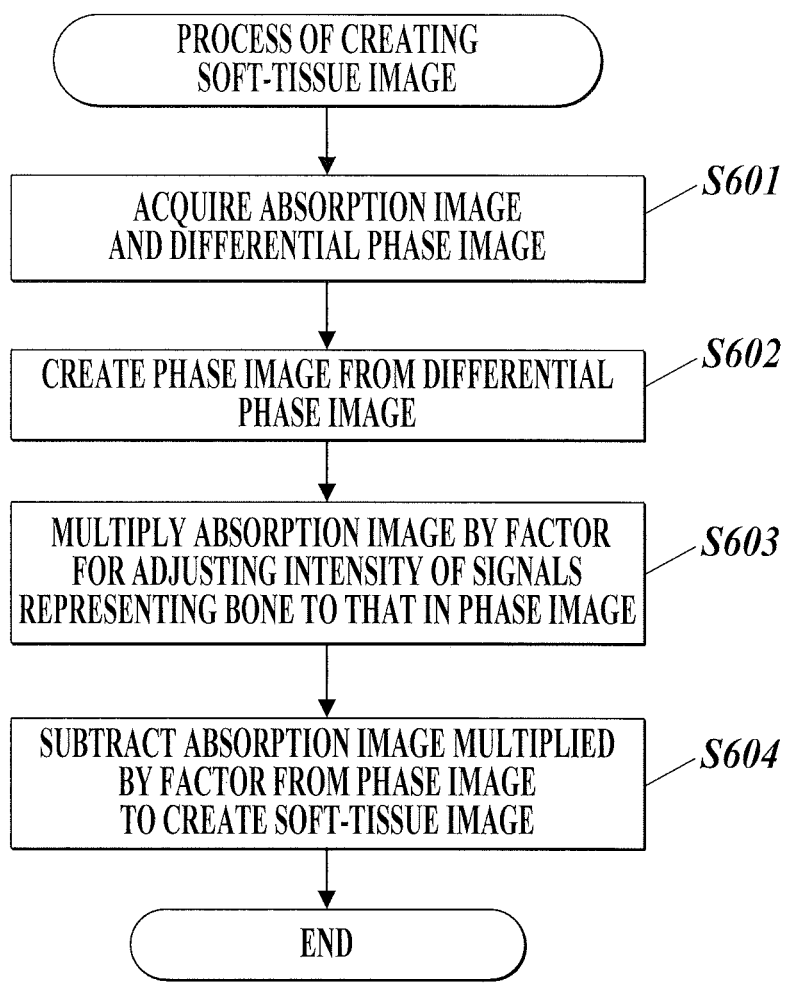

MEDICAL IMAGING SYSTEM AND MEDICAL IMAGE PROCESSING APPARATUS

CROSS REFERENCE TO RELATED APPLICATIONS

This is the U.S. national stage of application No. PCT/JP2013/062690, filed on 1 May 2013. Priority under 35 U.S.C. §119 (a) and 35 U.S.C. §365(b) is claimed from Japanese Application No. 2012-131596, filed 11 Jun. 2012, the disclosure of which is also incorporated herein by reference.

TECHNICAL FIELD

The present invention relates to a medical imaging system and a medical image processing apparatus.

BACKGROUND ART

Most of the medical X-ray images for diagnosis are created through absorption contrast imaging. In the absorption contrast imaging, the contrast is defined by differences in attenuation of the intensity of X rays that passed a subject. In contrast, in phase contrast imaging, the contrast is defined by phase shifts in X rays instead of absorption of the X rays.

For example, Patent Literature 1 discloses an X-ray imaging system to create an X-ray image with a high level of visibility through the edge enhancement utilizing the refraction of X rays in a magnified imaging operation. Patent Literature 1 also discloses the superimposition of a phase contrast image on an absorption contrast image.

Patent Literature 2 discloses the creation of a phase contrast image through tomography and the superimposition of the phase contrast image obtained by tomography on an absorption image created through tomography in the field of computerized tomography (CT).

CITATION LIST

Patent Literature

Patent Literature 1: Japanese Patent Laid-open Publication No. 2003-93377
Patent Literature 2: Japanese Unexamined Patent Application Publication (Translation of PCT Application) No. 2009-525084

SUMMARY OF INVENTION

Problems to be Solved by Invention

In the phase contrast image disclosed in Patent Literature 1, the edge of a subject has enhanced contrast and thus has increased visibility. However, the image signals in the vicinity of the edge of the subject are distorted, so that the image cannot depict the actual shape in the vicinity of the edge. In addition, this method requires two imaging operations at different magnifications for a phase contrast image (by magnified imaging) and an absorption contrast image (by contact imaging), and requires the adjustment of the magnification and the alignment of these images through the enlargement accompanying interpolation or the contraction.

In contrast, the technique disclosed in Patent Literature 2 does not require the adjustment of the magnification or the alignment through the enlargement accompanying interpolation or the contraction, because a phase contrast image and an absorption contrast image to be superimposed are acquired in a single imaging operation. However, a CT system has a complicated configuration and thus cannot be readily introduced.

Patent Literature 2 discloses that a combined image created by superimposing a phase contrast image on an absorption contrast image is effective for the diagnosis in the structure of a junction between a bone and a cartilage. However, Patent Literature 2 does not disclose the type of combined image or the image display mode that is effective for a diagnosis target site and/or a target disease to be inspected in the target site.

An object of the invention is to facilitate early diagnosis and improve the diagnostic accuracy through the selection of an image display mode effective for the diagnosis depending on the diagnosis target site and/or the type of disease.

Means for Solving Problems

To solve the above problems, according to a first aspect of the present invention, there is provided a medical imaging system to create three kinds of reconstructed images of a diagnosis target site in a subject through X-ray imaging of the diagnosis target site with a Talbot or Talbot-Lau imaging apparatus, the three kinds of reconstructed images being an absorption image, a differential phase image, and a small-angle scattering image, the medical imaging system including: an input unit to receive an input of diagnosis target information for specifying the diagnosis target site, or the diagnosis target site and a disease to be diagnosed in the diagnosis target site; and a control unit to create a combined image of two kinds of reconstructed images among the three kinds of reconstructed images on the basis of the diagnosis target information input through the input unit, and to control a displaying unit to display the combined image.

Preferably, one of the two kinds of reconstructed images is the absorption image.

Preferably, the control unit processes at least one of the two kinds of reconstructed images and then creates the combined image.

Preferably, the control unit creates a combined image in which a signal representing a structure common to the differential phase image and the absorption image is removed or attenuated through the following process: processing the absorption image into a differential absorption image, multiplying the differential absorption image by a factor for adjusting an intensity of a signal representing a structure in the differential absorption image to an intensity of a signal representing the structure in the differential phase image, the structure being common to the differential phase image and the differential absorption image, and subtracting the differential absorption image multiplied by the factor from the differential phase image, or processing the differential phase image into a phase image, multiplying the absorption image by a factor for adjusting an intensity of a signal representing a structure in the absorption image to an intensity of a signal representing the structure in the phase image, the structure being common to the phase image and the absorption image, and subtracting the absorption image multiplied by the factor from the phase image.

Preferably, the control unit creates two or more combined images and controls the displaying unit to simultaneously or alternately display the two or more combined images.

Preferably, the control unit controls the displaying unit to simultaneously or alternately display the combined image and at least one of the three kinds of reconstructed images.

Preferably, the control unit further creates a combined image of the three kinds of reconstructed images, and controls the displaying unit to simultaneously or alternately display the combined image of the two kinds of reconstructed images and the combined image of the three kinds of reconstructed images.

Preferably, the diagnosis target site is breasts.

According to a second aspect of the present invention, there is provided a medical image processing apparatus including: a reconstructed-image creating unit to at least create a differential phase image and an absorption image of three kinds of reconstructed images on the basis of an image signal of a subject acquired with an X-ray imaging apparatus including a Talbot or Talbot-Lau interferometer, the three kinds of reconstructed images being the absorption image, the differential phase image, and a small-angle scattering image; and a combining unit to create a combined image in which a signal representing a structure common to the differential phase image and the absorption image is removed or attenuated through the following process: processing the absorption image into a differential absorption image, multiplying the differential absorption image by a factor for adjusting an intensity of a signal representing a structure in the differential absorption image to an intensity of a signal representing the structure in the differential phase image, the structure being common to the differential phase image and the differential absorption image, and subtracting the differential absorption image multiplied by the factor from the differential phase image, or processing the differential phase image into a phase image, multiplying the absorption image by a factor for adjusting an intensity of a signal representing a structure in the absorption image to an intensity of a signal representing the structure in the phase image, the structure being common to the phase image and the absorption image, and subtracting the absorption image multiplied by the factor from the phase image.

Preferably, the combining unit calculates a ratio of the signals representing the common structure between the two images used for the subtraction, and uses the ratio as the factor.

Preferably, the medical image processing apparatus further includes a storage unit to store a threshold corresponding to at least one of the absorption image, the differential absorption image, the phase image, the differential phase image, and the small-angle scattering image, and the combining unit compares a pixel value or an absolute pixel value of a corresponding one of the images created by the reconstructed-image creating unit with the threshold, reduces the factor for a region having a pixel value not exceeding the threshold, and then creates the combined image.

Preferably, the medical image processing apparatus further includes: a displaying unit to display the combined image; and an operating unit used for changing the factor and/or the threshold, the combining unit changes the factor and/or the threshold in response to an operation to the operating unit and then re-creates a combined image, and the displaying unit displays the combined image re-created based on the changed factor and/or threshold.

Preferably, the medical image processing apparatus further includes a correcting unit to correct an artifact in the differential phase image caused by an imaging condition in the X-ray imaging apparatus, and the combining unit creates the combined image with the differential phase image corrected by the correcting unit.

Effects of Invention

The present invention can facilitate early diagnosis and improve the diagnostic accuracy through the selection of an image display mode effective for the diagnosis depending on the diagnosis target site and/or the type of disease.

BRIEF DESCRIPTION OF THE DRAWINGS

FIG. 13 is a flowchart illustrating an image displaying process executed by the control unit illustrated in FIG. 2 in the diagnosis in breasts;

FIG. 19 is a flowchart illustrating a process of creating a differential soft-tissue image executed by the control unit illustrated in FIG. 2 according to a second embodiment; and FIG. 20 is a flowchart illustrating a process of creating a soft-tissue image executed by the control unit illustrated in FIG. 2 according to a third embodiment.

MODES FOR CARRYING OUT THE INVENTION

[First Embodiment]

A first embodiment of the invention will now be described with reference to the drawings.

Figure 1A:
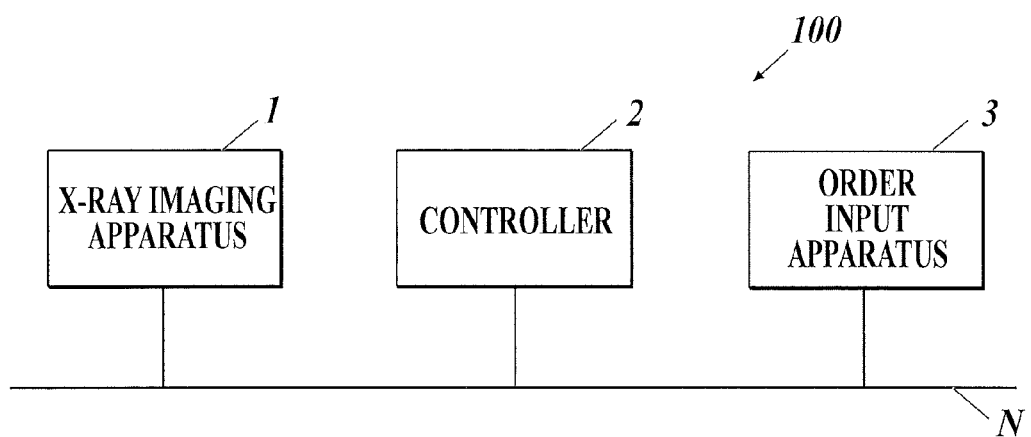
FIG. 1A illustrates the entire configuration of a medical imaging system according to this embodiment.

FIG. 1A illustrates the entire configuration of a medical imaging system 100 according to the embodiment.

The medical imaging system 100 includes an X-ray imaging apparatus 1, a controller 2, and an order input apparatus 3.

The X-ray imaging apparatus 1 is connected to the controller 2 via a communication network N such as a local area network (LAN) for mutual data transmission therebetween. The controller 2 is also connected to the order input apparatus 3 via the communication network N for mutual data transmission therebetween.

The X-ray imaging apparatus 1 includes a known Talbot or Talbot-Lau interferometer, which acquires moire images for creating reconstructed images of a subject.

Figure 1B:
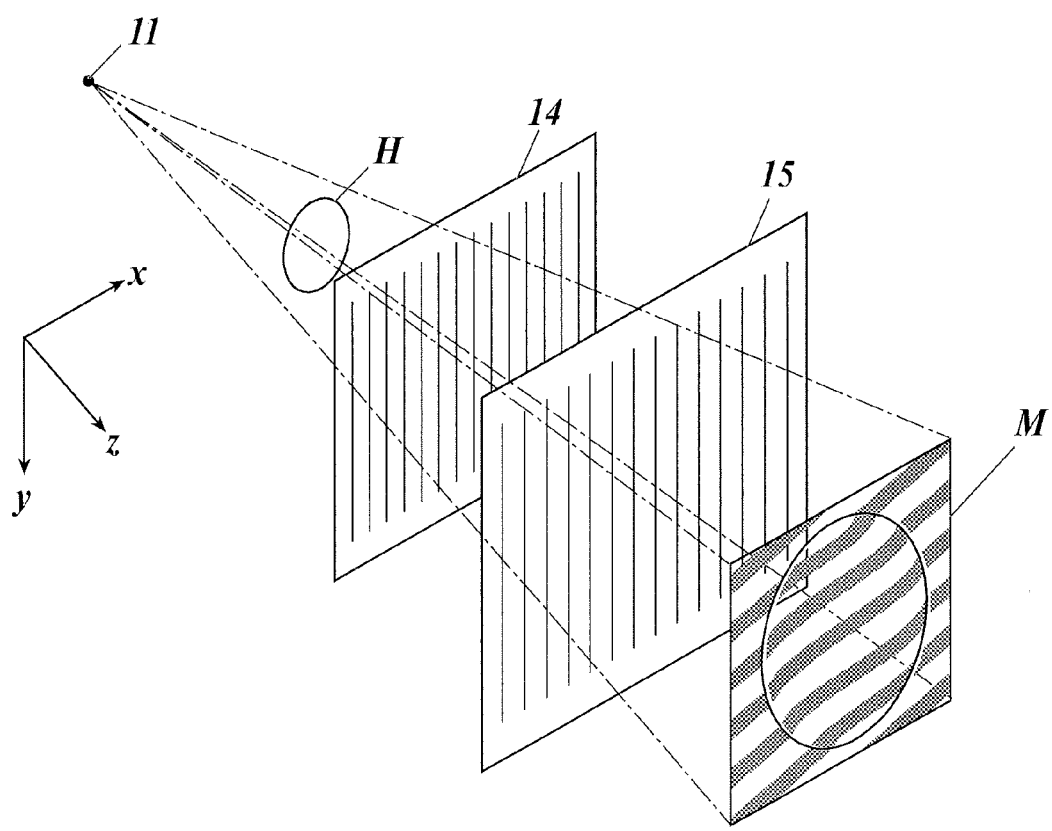
FIG. 1B illustrates the principle of a Talbot interferometer.

As is disclosed in International Publication Nos. WO 2004/058070 (Known Literature 1), WO 2011/033798 (Known Literature 2), and WO 2011/114845 (Known Literature 3), for example, the Talbot interferometer and Talbot-Lau interferometer acquire moire images for creating reconstructed images of a subject by the Talbot effect. The Talbot effect indicates a phenomenon of coherent light (X rays emitted from an X-ray source 11) passing through a first lattice 14 having slits aligned at certain intervals and forming images of the lattice in a certain cycle in the traveling direction of the light (z direction), as illustrated in FIG. 1B. The lattice images are called self-images. The Talbot interferometer further includes a second lattice 15 disposed at a position of a formed self-image in parallel with the first lattice 14, and observes interference fringes (moire) M generated by inclining the second lattice 15 about its optical axis (the line connecting the focus of the X rays and the center of the lattice) with respect to the first lattice 14. In the imaging operation by a fringe scanning method, the relative angle of the second lattice 15 from the first lattice 14 may be 0°. A subject H is disposed in front of or behind the first lattice 14 because any object in front of the second lattice 15 will disturb the moire M. The subject H is irradiated with coherent X rays to form images of the moire M, which are then processed to create reconstructed images of the subject H.

The Talbot interferometer includes an X-ray source 11, a first lattice 14 disposed substantially perpendicular to the direction of propagating X-rays, a second lattice 15, and a radiation detector (not illustrated). The first lattice 14 and the second lattice 15 are diffraction gratings and each have a plurality of slits aligned in the direction (x direction) perpendicular to the direction of propagating X-rays (z direction). In the Talbot interferometer, a subject H is disposed between the X-ray source 11 and the first lattice 14 or between the first lattice 14 and the second lattice 15. The first lattice 14 and the second lattice 15 are relatively shifted by a certain period (distance), and then the radiation detector reads image signals in response to the X rays emitted from the X-ray source 11 every shift by the certain distance. Through the repetition of these steps, a plurality of moire images for the fringe scanning method are acquired.

In contrast to the Talbot interferometer, the Talbot-Lau interferometer further includes a multi-slit element (not illustrated) at a position closer to the X-ray source 11 between the X-ray source 11 and the first lattice 14. The multi-slit element is a diffraction grating, and has a plurality of slits aligned perpendicular to the direction of propagating X-rays, like the first lattice 14 and the second lattice 15. In the Talbot-Lau interferometer, a subject H is disposed between the multi-slit element and the first lattice 14. The multi-slit element is shifted relative to the first lattice 14 and the second lattice 15 by a certain period (distance), and then the radiation detector reads image signals in response to the X rays emitted from the X-ray source 11 every shift by the certain distance. Through the repetition of these steps, a plurality of moire images for the fringe scanning method are acquired.

The method of acquiring a plurality of moire images for the fringe scanning method in the X-ray imaging apparatus 1 (Talbot or Talbot-Lau interferometer) is called the fringe scanning method.

Alternatively, the Talbot or Talbot-Lau interferometer may emit X rays only once without shifting the first lattice 14, the second lattice 15, which defines a predetermined relative angle from the first lattice 14, or the multi-slit element, and then the radiation detector may read image signals in response to the emitted X rays to acquire a moire image, as is disclosed in Known Literature 4 (International Publication No. WO 2012/029340), for example. This method of acquiring a moire image is called the Fourier transform technique.

The controller 2 is a medical image processing apparatus that creates three kinds of reconstructed images (an absorption image, a differential phase image, and a small-angle scattering image) of a subject from the moire images acquired by the X-ray imaging apparatus 1, creates a combined image of two of the three reconstructed images on the basis of the target site and the disease, and displays the combined image.

Figure 2:
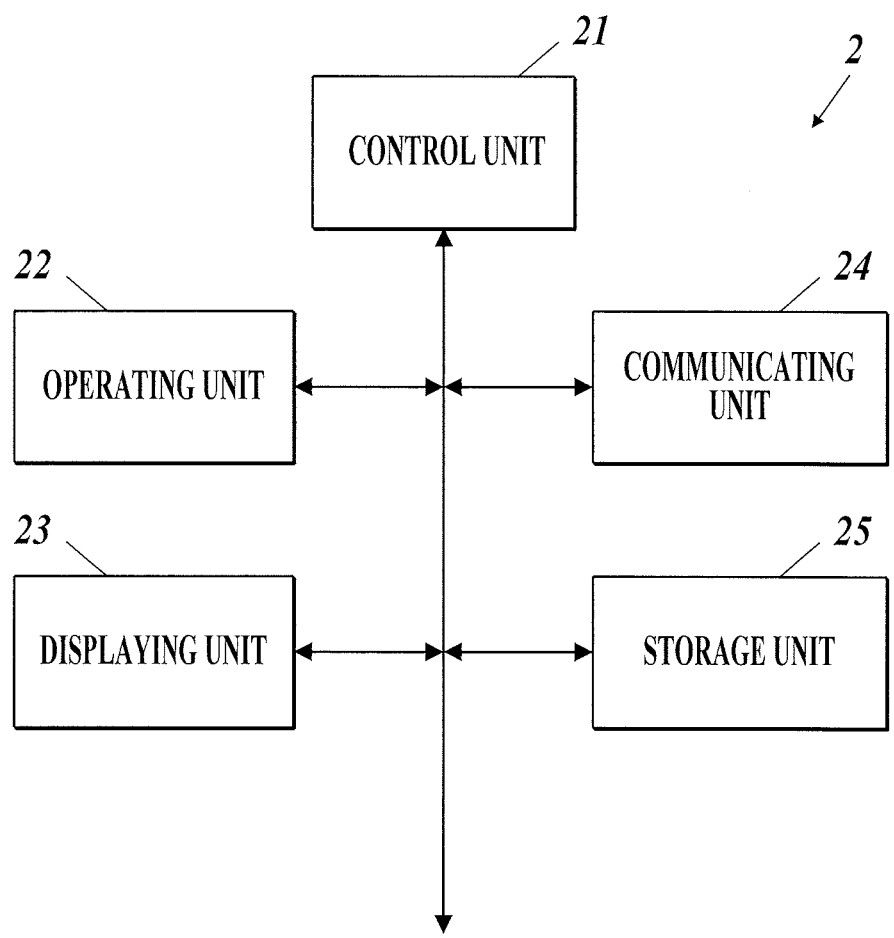
FIG. 2 is a block diagram illustrating the functional configuration of the controller illustrated in FIG. 1A.

With reference to FIG. 2, the controller 2 includes a control unit 21, an operating unit 22, a displaying unit 23, a communicating unit 24, and a storage unit 25.

The control unit 21 includes a central processing unit (CPU) or a random access memory (RAM). The control unit 21 executes various processes such as an image creating and displaying process (described below), in cooperation with programs stored in the storage unit 25.

The operating unit 22 includes a keyboard including cursor keys, numeric input keys, and various functional keys, and a pointing device such as a mouse. The operating unit 22 transmits input signals, which contain signals from pressed keys in the keyboard and signals from the operated mouse, to the control unit 21. Alternatively, the operating unit 22 may include a touch panel integrated with a display of the displaying unit 23, and generate signals in response to an operation on the touch panel to transmit the signals to the control unit 21.

The displaying unit 23 includes a monitor, such as a cathode ray tube (CRT) or a liquid crystal display (LCD). The displaying unit 23 displays an operation screen, an operational state of the X-ray imaging apparatus 1, and created reconstructed images and combined images, under the display control from the control unit 21.

The communicating unit 24 includes a communication interface to communicate with the X-ray imaging apparatus 1 and the order input apparatus 3 in the communication network N through a wired or wireless means. For example, the communicating unit 24 receives imaging order information from the order input apparatus 3, transmits imaging conditions and control signals to the X-ray imaging apparatus 1, and receives moire images from the X-ray imaging apparatus 1.

The storage unit 25 stores programs to be executed by the control unit 21 and data required for the execution of the programs.

For example, the storage unit 25 stores the imaging order information transmitted from the order input apparatus 3. The imaging order information contains the date of imaging, the name of a patient, and diagnosis target information (information on a diagnosis target site (site to be imaged), or on the diagnosis target site and a disease to be diagnosed in the site).

The storage unit 25 also stores an imaging condition table associating the diagnosis target information with imaging conditions suitable for the imaging of the diagnosis target.

The storage unit 25 also stores a combined image table associating the diagnosis target information with information on types of images (including combined images) and an image display mode that are suitable for the diagnosis target.

The storage unit 25 also stores three kinds of reconstructed images created on the basis of the moire images transmitted from the X-ray imaging apparatus 1, combined images, information on the type of the calculation (addition, subtraction, multiplication, or division) used for the creation of the combined images, image processing parameters, and display parameters, such as gray scale correction and positions of image scaling, in conjunction with the imaging order information.

Furthermore, the storage unit 25 stores data, such as gain correction data and a defective pixel map, corresponding to the radiation detector in the X-ray imaging apparatus 1 in advance. Alternatively, the X-ray imaging apparatus 1 may store the data, and transmit the moire images after various corrections based on the data to the controller 2.

The order input apparatus 3 generates imaging order information in response to the input from an operator. The order input apparatus 3 can use a hospital information system (HIS) or a radiology information system (RIS), for example.

The operations of the medical imaging system 100 will now be explained.

Figure 3:
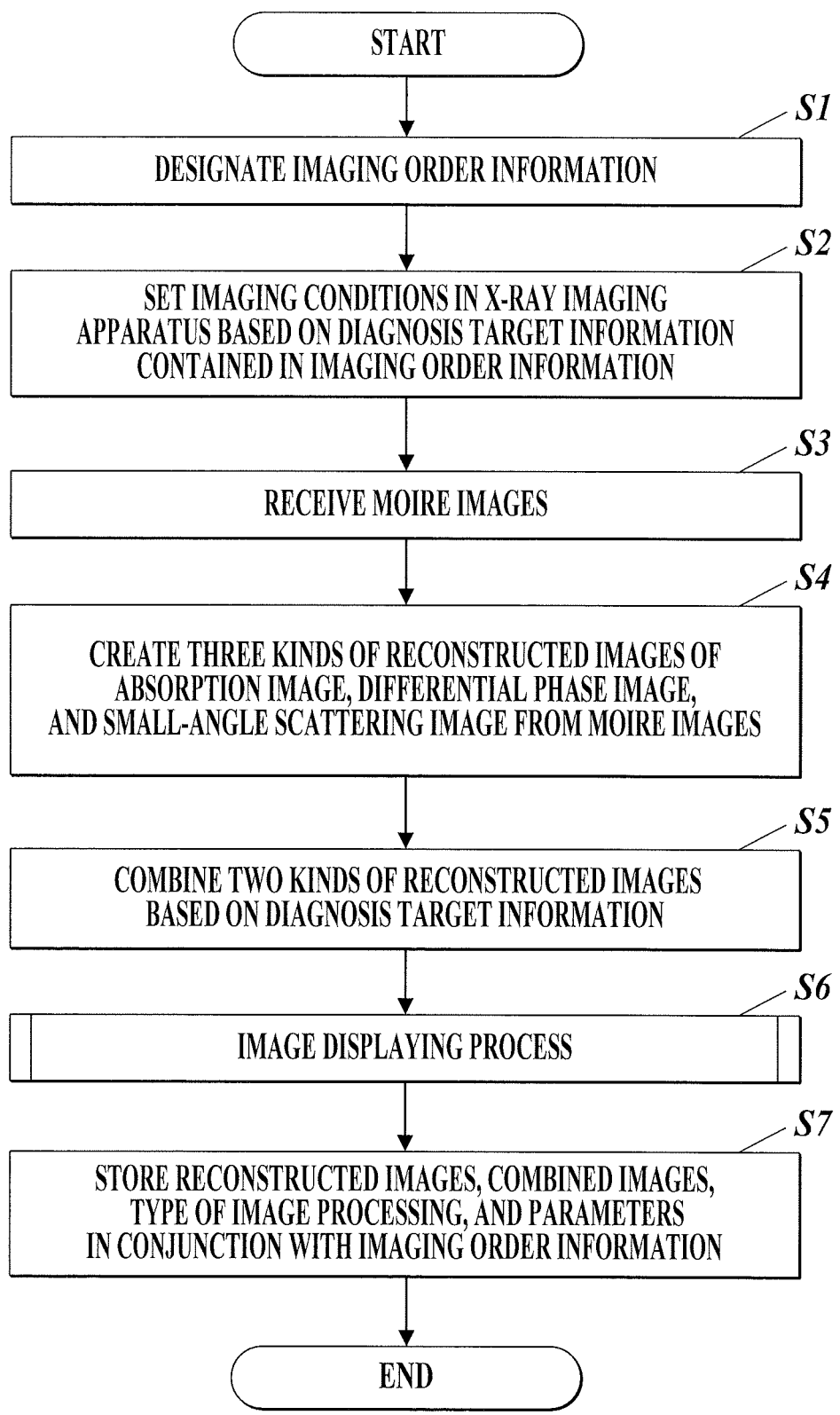
FIG. 3 is a flowchart illustrating an image creating and displaying process executed by the control unit illustrated in FIG. 2.

FIG. 3 is a flowchart illustrating an image creating and displaying process executed by the control unit 21 of the controller 2. The image creating and displaying process is executed in cooperation with the control unit 21 and the programs stored in the storage unit 25 in response to an operation to the operating unit 22.

The displaying unit 23 of the controller 2 displays a list of pieces of imaging order information, and one of the pieces of imaging order information for an imaging object is designated through the operating unit 22 (Step S1).

Imaging conditions associated with the diagnosis target information contained in the designated imaging order information are then read from the imaging condition table stored in the storage unit 25, and are transmitted to the X-ray imaging apparatus 1 by the communicating unit 24 to be set in the X-ray imaging apparatus 1 (Step S2).

In response to the reception of the imaging conditions from the controller 2, the X-ray imaging apparatus 1 captures X-ray images with the subject and an X-ray image without the subject on the basis of the received imaging conditions, to acquire one or more moire images with the subject and a moire image without the subject. The acquired moire images with the subject and moire image without the subject are transmitted to the controller 2.

When the communicating unit 24 receives the moire images from the X-ray imaging apparatus 1 (Step S3), three kinds of reconstructed images (an absorption image, a differential phase image, and a small-angle scattering image) of the subject are created from the received moire images (Step S4).

Figure 4A:
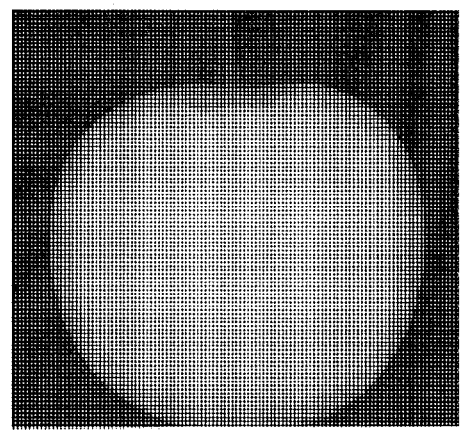
FIG. 4A illustrates an example absorption image of a cherry as a subject.
Figure 4B:
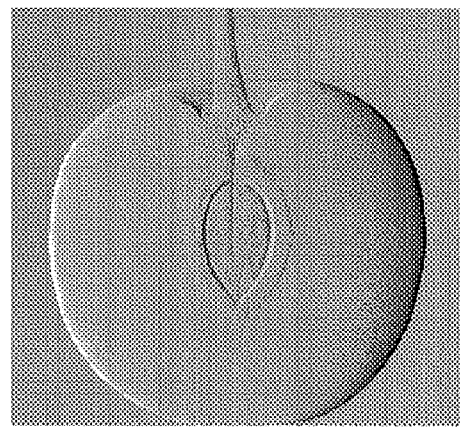
FIG. 4B illustrates an example differential phase image of a cherry as a subject.
Figure 4C:
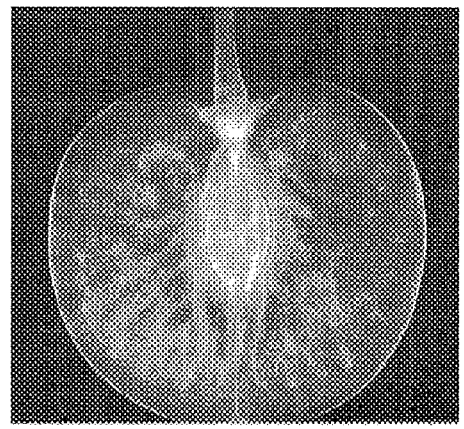
FIG. 4C illustrates an example small-angle scattering image of a cherry as a subject.

FIGS. 4A to 4C respectively illustrate an example absorption image, differential phase image, and small-angle scattering image of a cherry as a subject.

The absorption image (X-ray absorption image) is created by imaging the average components of interference fringes and has contrast reflecting the X-ray attenuation caused by the subject. The absorption image has been used for conventional diagnosis and is familiar to healthcare workers such as medical doctors. The absorption image is advantageous to depict bone that can readily create clear X-ray absorption contrast (refer to FIG. 4A).

The differential phase image is created by imaging phase information on the interference fringes and has contrast reflecting the tilt of the X-ray wavefront caused by the subject. The differential phase image is superior in the depiction of soft tissue to the absorption image (refer to FIG. 4B).

The small-angle scattering image is created by imaging the visibility of the interference fringes and has contrast reflecting the X-ray dispersion occurring in the subject (refer to Known Literature 5: Distribution of unresolvable anisotropic microstructures revealed in visibility-contrast images using x-ray Talbot interferometry; Wataru Yashiro et al.; PHYSICAL REVIEW B 84; 094106 (2011)). The small-angle scattering image is superior in the depiction of fine structures to the absorption image (refer to FIG. 4C).

The absorption image, the differential phase image, and the small-angle scattering image are created in Step S4 from the same one or more moire images (group of images) transmitted from the X-ray imaging apparatus 1. The three reconstructed images thus depict the identical portion of the identical subject and do not need alignment of the subjects among the images.

The three kinds of reconstructed images can be created through a known procedure, such as a technique disclosed in Known Literature 4.

The one or more moire images with the subject and the moire images without the subject are subjected to corrections of the offset, gain, defective pixels, and variations in X-ray intensity. From the corrected moire images with the subject, three kinds of reconstructed images (an absorption image, a differential phase image, and a small-angle scattering image) with the subject are created. From the corrected moire images without the subject, three kinds of reconstructed images (an absorption image, a differential phase image, and a small-angle scattering image) without the subject are created.

In specific, if the X-ray imaging apparatus 1 creates moire images for fringe scanning by a fringe scanning method, the absorption image is created through the addition of the interference fringes of the plural moire images. The differential phase image is created through the calculation of the phase of the interference fringes on the basis of the principle of the fringe scanning method. The small-angle scattering image is created through the calculation of the visibility (visibility=amplitude/average value) of the interference fringes on the basis of the principle of the fringe scanning method.

If the X-ray imaging apparatus 1 creates moire images by a Fourier transform technique, the corrected moire image with the subject and the corrected moire image without the subject are each subjected to the Fourier transform computation (two-dimensional Fourier transform computation) to extract the zero-order component and the first-order component shifted by a carrier frequency (=moire frequency) through a Hanning window. The extracted zero- and first-order components are then each subjected to the inverse Fourier transform computation. The absorption image is created from the amplitude of the zero-order component, the differential phase image is created from the phase of the first-order component, and the small-angle scattering image is created from the ratio of the amplitudes of the zero-order component to the first-order component (=visibility).

The resulting reconstructed images without the subject are applied to the corresponding reconstructed images with the subject (e.g., the small-angle scattering image without the subject is applied to the small-angle scattering image with the subject) to remove the phase of the interference fringes and correct the unevenness in the image. This process completes the creation of three kinds of reconstructed images for diagnosis.

A combined image is then created with at least two of the three kinds of reconstructed images on the basis of the diagnosis target information contained in the imaging order information (Step S5). It is noted that two or more types of combined images may also be created.

In this step, the combined image table stored in the storage unit 25 is read, and a combined image of the type that is associated with the diagnosis target information contained in the imaging order information in the combined image table is created.

The combined image can be created through addition, subtraction, division, or multiplication of the corresponding pixel values between at least two of the three kinds of reconstructed images.

Figure 5A:
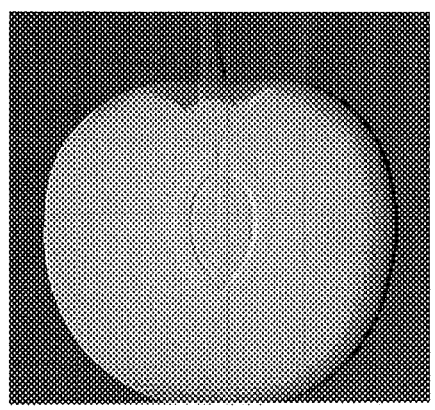
FIG. 5A illustrates a combined image created by adding the differential phase image illustrated in FIG. 4B to the absorption image illustrated in FIG. 4A.
Figure 5B:
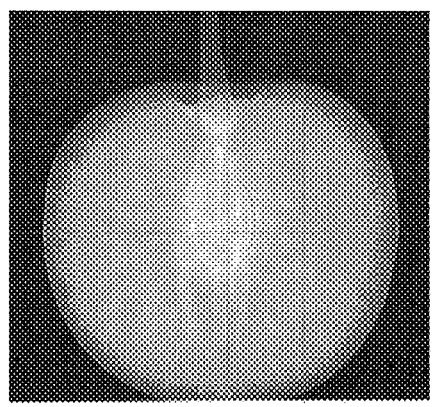
FIG. 5B illustrates a combined image created by adding the small-angle scattering image illustrated in FIG. 4C to the absorption image illustrated in FIG. 4A.
Figure 5C:
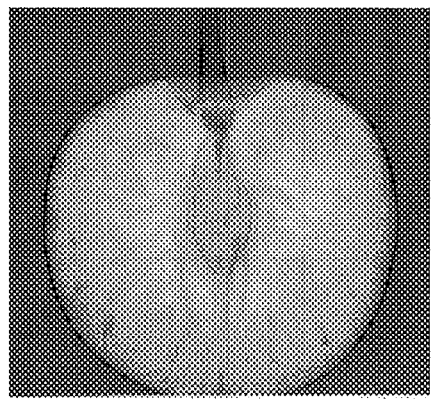
FIG. 5C illustrates a combined image created by subtracting the small-angle scattering image illustrated in FIG. 4C from the absorption image illustrated in FIG. 4A.
Figure 5D:
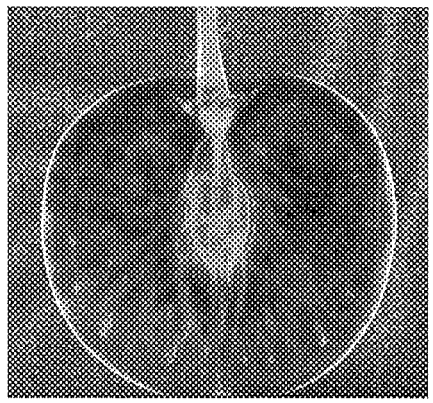
FIG. 5D illustrates a combined image created by dividing the small-angle scattering image illustrated in FIG. 4C by the absorption image illustrated in FIG. 4A.

FIG. 5A illustrates an example combined image created by adding the differential phase image illustrated in FIG. 4B to the absorption image illustrated in FIG. 4A. FIG. 5B illustrates an example combined image created by adding the small-angle scattering image illustrated in FIG. 4C to the absorption image illustrated in FIG. 4A. FIG. 5C illustrates an example combined image created by subtracting the small-angle scattering image illustrated in FIG. 4C from the absorption image illustrated in FIG. 4A. FIG. 5D illustrates an example combined image created by dividing the small-angle scattering image illustrated in FIG. 4C by the absorption image illustrated in FIG. 4A.

With reference to FIGS. 5A to 5D, different operations (addition, subtraction, division, and multiplication) can create combined images having different characteristics. The operation to be used is stored in the combined image table in conjunction with the diagnosis target information in advance.

Table 1 shows the results of sensory evaluation by sight of the performance of the diagnosis based on the individual observations of an absorption image, a differential phase image, and a small-angle scattering image, and the diagnosis based on the individual or comparative observations of a combined image of the absorption image and the differential phase image and a combined image of the absorption image and the small-angle scattering image, for the respective targets to be inspected for the diagnosis of joint diseases and breast cancer. In Table 1, the evaluation "A" indicates the image depicting the target sufficiently for the diagnosis, whereas the evaluation "A⁻" indicates the combined image possibly having reduced diagnostic performance depending on the type of combining operation compared to that in an individual reconstructed image. The reduction in the diagnostic performance occurs if the combining operation causes an increase in the noise that is more influential than the increase in the contrast of an object of interest or generates any signal obstructive to the diagnosis. It is noted that the diagnostic performance can be increased comparable to that in the individual reconstructed image through a device in the combining operation, such as changes in the contribution rates of the reconstructed images in response to their image densities or a reduction in the contribution rate of a flat region having small signal variations in each reconstructed image. The evaluation "B" indicates the image depicting the target visibly but less clearly than the image evaluated as "A" (the image alone being insufficient for the diagnosis or possibly leading to oversight of a disease), whereas the evaluation "D" indicates the image not depicting the target site. The evaluations "A" "A⁻" "B" and "D" are based on the comparison of the images in the column in Table 1 other than the comparison of the items in the row. Table shows the evaluation results of example combined images respectively created by adding the differential phase image to the absorption image, and the small-angle scattering image to the absorption image.

The contribution rate indicates the degree of contribution of each reconstructed image (or parts or some pixels of the image) to the combined image. For example, the contribution rate includes a weighting factor of each reconstructed image in the combined image created through the addition or subtraction.

TABLE 1

| | \multicolumn{5}{c}{JOINT DISEASES} |
| --- | --- | --- | --- | --- | --- |
| | CARTILAGE | TENDON | BONE | MICRO-FRACTURE | TRABECULAR FINE STRUCTURE |
| ABSORPTION IMAGE | D | D | A | D | D |
| | \multicolumn{5}{c}{EFFECTIVE IN BONE DIAGNOSIS} |
| DIFFERENTIAL PHASE IMAGE | A | A | B | D | D |
| | \multicolumn{5}{c}{EFFECTIVE IN SOFT TISSUE DIAGNOSIS} |
| SMALL-ANGLE SCATTERING IMAGE | D | D | B | A | A RECOGNIZABLE FINE STRUCTURES |
| | \multicolumn{5}{c}{EFFECTIVE IN ANALYSIS OF TRABECULAR FINE STRUCTURE AND MICROFRACTURE DIAGNOSIS} |
| COMBINED IMAGE OF DIFFERENTIAL PHASE IMAGE AND ABSORPTION IMAGE | $A^-$ | $A^-$ | $A^-$ | D | D |
| | \multicolumn{5}{c}{BONE AND SOFT TISSUE OBSERVABLE SIMULTANEOUSLY COMBINED IMAGE WITH CONVENTIONAL ABSORPTION IMAGE IS FAMILAR TO MEDICAL DOCTORS AND TECHNOLOGISTS} |
| COMBINED IMAGE OF SMALL-ANGLE SCATTERING IMAGE AND ABSORPTION IMAGE | D | D | $A^-$ | $A^-$ | $A^-$ |
| | \multicolumn{5}{c}{EFFECTIVE IN OSTEOPOROSIS AND MICROFRACTURE DIAGNOSIS COMBINED IMAGE WITH CONVENTIONAL ABSORPTION IMAGE IS FAMILIAR TO MEDICAL DOCTORS AND TECHNOLOGISTS} |
| COMPARISON BETWEEN TWO COMBINED IMAGES | — | | | | |

| | \multicolumn{3}{c}{BREAST CANCER SCREENING} |
| --- | --- | --- | --- |
| | TUMOR | SPECULATION | MICRO-CALCIFICATION |
| ABSORPTION IMAGE | B DIFFICULT TO DIAGNOSE | B | B |
| | \multicolumn{3}{c}{DIFFICULT TO DIAGNOSE TUMOR} |
| DIFFERENTIAL PHASE IMAGE | B DIFFICULT TO DIAGNOSE | A | B |
| | \multicolumn{3}{c}{EFFECTIVE SPECULATION OBSERVATION DIFFICULT TO DIAGNOSE TUMOR} |
| SMALL-ANGLE SCATTERING IMAGE | B DIFFICULT TO DIAGNOSE | B | A |
| | \multicolumn{3}{c}{EFFECTIVE IN MICROCALCIFICATION OBSERVATION DIFFICULT TO DIAGNOSE TUMOR} |
| COMBINED IMAGE OF DIFFERENTIAL PHASE IMAGE AND ABSORPTION IMAGE | A CLEARER TUMOR EDGE | $A^-$ | B |
| | \multicolumn{3}{c}{CLEARLY DEPICTED TUMOR EDGE AND SPECULATION STRUCTURE COMBINED IMAGE WITH FAMILIAR CONVENTIONAL ABSORPTION IMAGE FACILITATES DETECTION OF TUMOR AND SPECULATION STRUCTURE} |
| COMBINED IMAGE OF SMALL-ANGLE SCATTERING IMAGE AND ABSORPTION IMAGE | A RECOGNIZABLE HOMOGENEITY OF INTERNAL STRUCTURE OF TUMOR | B | $A^-$ |
| | \multicolumn{3}{c}{EFFECTIVE IN ESTIMATION OF INTERNAL STRUCTURE OF TUMOR AND DETECTION OF FAINT MICROCALCIFICATION ESCAPABLE IN ABSORPTION IMAGE} |
| COMPARISON BETWEEN TWO COMBINED IMAGES | \multicolumn{3}{l}{MORE ACCURATE DIAGNOSIS THROUGH COMPREHENSIVE INSPECTION OF EDGE AND INTERNAL STRUCTURE OF TUMOR, SPECULATION, AND MICROCALCIFICATION} |

As shown in Table 1, with respect to the diagnosis target items (cartilage, tendon, bone, a microfracture, and trabecular fine structures) for the diagnosis of joint diseases, the absorption image depicts only bone sufficiently for the diagnosis. The differential phase image depicts cartilage and tendon sufficiently for the diagnosis, and thus is effective in the inspection of soft tissue. The small-angle scattering image depicts a microfracture and trabecular fine structures sufficiently for the diagnosis, and thus is effective in the analysis of the trabecular fine structures and the diagnosis of a microfracture.

Figure 6A:
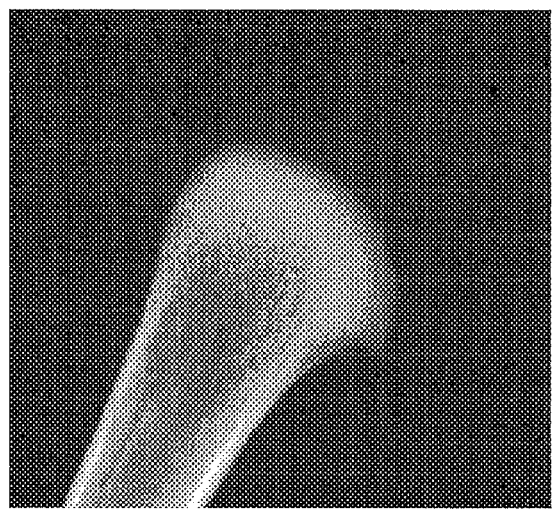
FIG. 6A illustrates an example absorption image of a fowl wing cartilage as a subject.
Figure 6B:
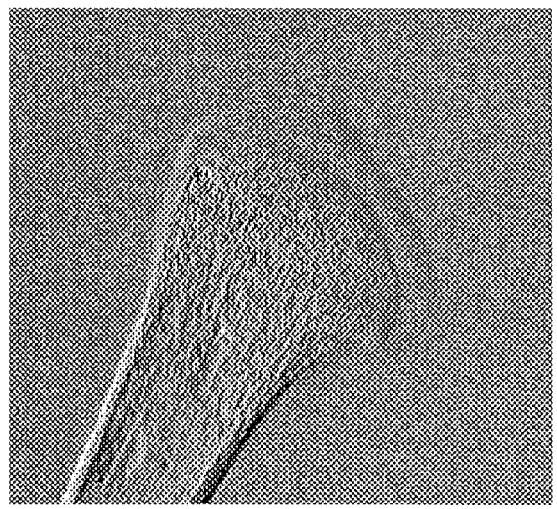
FIG. 6B illustrates an example differential phase image of a fowl wing cartilage as a subject.
Figure 6C:
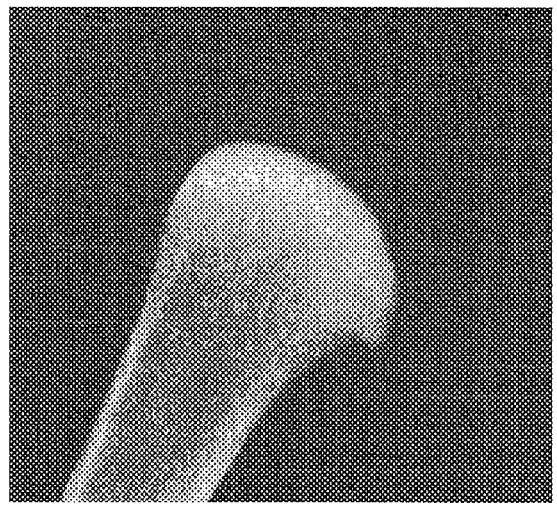
FIG. 6C illustrates an example small-angle scattering image of a fowl wing cartilage as a subject.
Figure 7A:
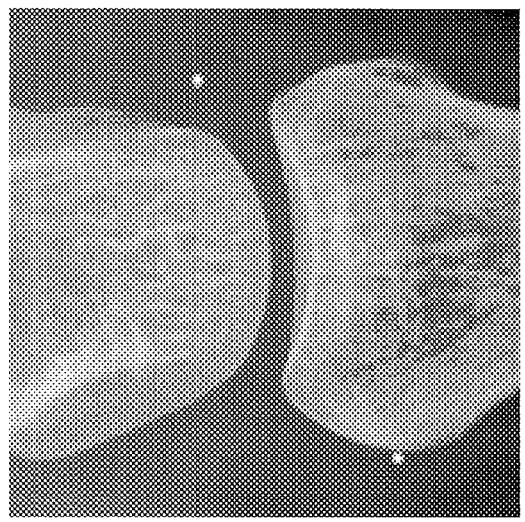
FIG. 7A illustrates an example absorption image of a wrist joint as a subject.
Figure 7B:
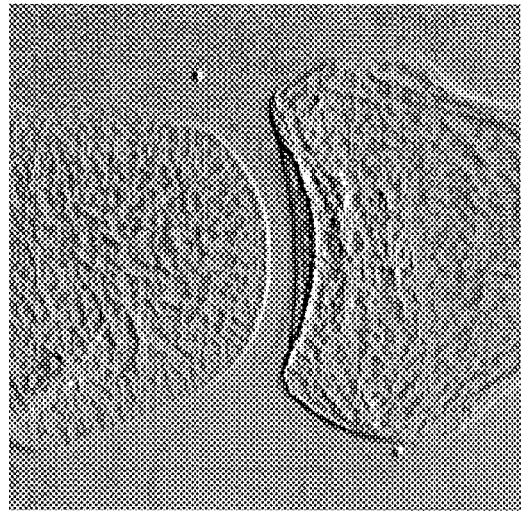
FIG. 7B illustrates an example differential phase image of a wrist joint as a subject.
Figure 7C:
FIG. 7C illustrates an example small-angle scattering image of a wrist joint as a subject.

FIG. 6A illustrates an absorption image of a fowl wing cartilage as a subject. FIG. 6B illustrates a differential phase image of the fowl wing cartilage as a subject. FIG. 6C illustrates a small-angle scattering image of the fowl wing cartilage as a subject. FIG. 7A illustrates an absorption image of a wrist joint as a subject. FIG. 7B illustrates a differential phase image of the wrist joint as a subject. FIG. 7C illustrates a small-angle scattering image of the wrist joint as a subject.

As shown in Table 1, the combined image of the absorption image and the differential phase image depicts cartilage, tendon, and bone sufficiently for the diagnosis. The bone and soft tissue, which cannot be accurately inspected at once based on either one of the absorption image and the differential phase image, can be accurately inspected at once based on the single combined image. The combined image, which is composed of the absorption image sufficiently depicting bone and being familiar to medical doctors and the differential phase image sufficiently depicting soft tissue, facilitates medical doctors unfamiliar with the differential phase image to diagnose joint diseases.

The combined image of the absorption image and the small-angle scattering image depicts bone, a microfracture, and trabecular fine structures sufficiently for the diagnosis. The bone has higher visibility than that in the small-angle scattering image alone. The combined image, which is composed of the absorption image familiar to medical doctors and the small-angle scattering image sufficiently depicting the distribution of trabecular fine structures and the presence of a microfracture, facilitates medical doctors unfamiliar with the small-angle scattering image to diagnose osteoporosis and a microfracture.

The combination of the absorption image and the differential phase image or small-angle scattering image is effective in an imaging apparatus including a one-dimensional lattice having slits aligned at certain intervals. In the apparatus including a one-dimensional lattice, the resulting differential phase image and small-angle scattering image have directivity, i.e., can detect a variation in a subject in the direction perpendicular to the lattice structure other than a variation in the subject in the vertical direction. Against this problem, the combination of the absorption image having no directivity with the differential phase image or small-angle scattering image can compensate for information missing in the differential phase image or small-angle scattering image, to facilitate specifying of a site of lesion.

Figure 8A:
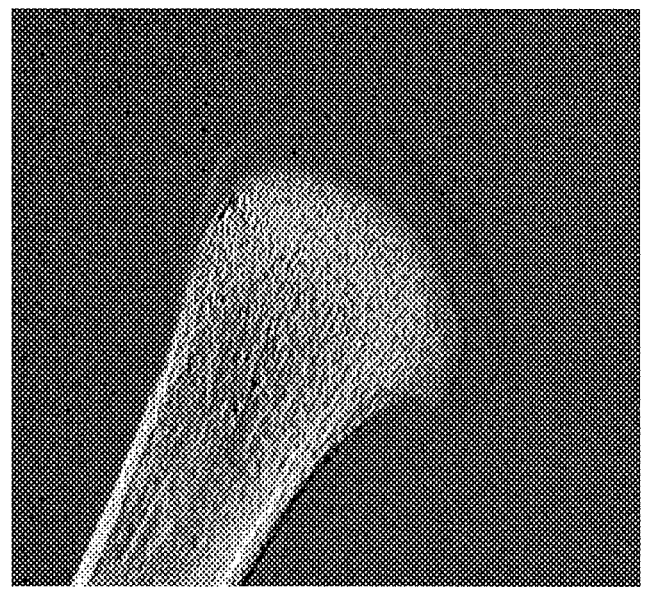
FIG. 8A illustrates a combined image (absorption image+differential phase image) of the absorption image of the fowl wing cartilage illustrated in FIG. 6A and the differential phase image of the fowl wing cartilage illustrated in FIG. 6B.

FIG. 8A illustrates a combined image (absorption image+differential phase image) of the absorption image of the fowl wing cartilage illustrated in FIG. 6A and the differential phase image of the fowl wing cartilage illustrated in FIG. 6B.

Figure 8B:
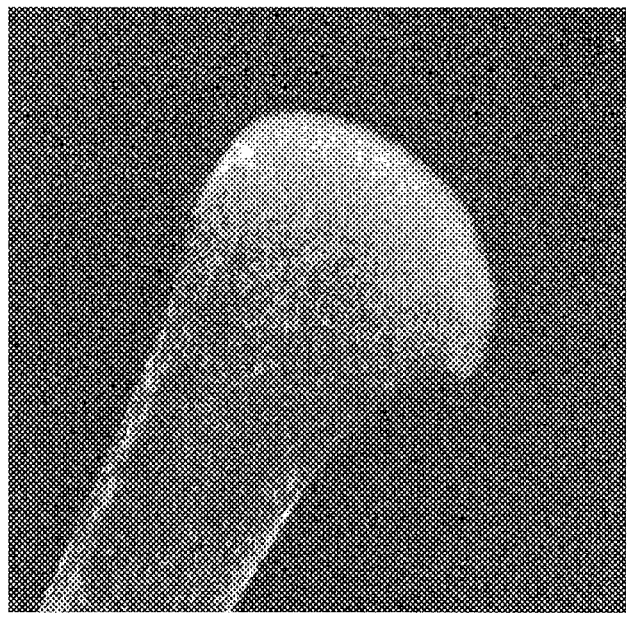
FIG. 8B illustrates a combined image (small-angle scattering image/absorption image) of the absorption image of the fowl wing cartilage illustrated in FIG. 6A and the small-angle scattering image of the fowl wing cartilage illustrated in FIG. 6C.

FIG. 8B illustrates a combined image (small-angle scattering image/absorption image) of the absorption image of the fowl wing cartilage illustrated in FIG. 6A and the small-angle scattering image of the fowl wing cartilage illustrated in FIG. 6C.

Figure 9A:
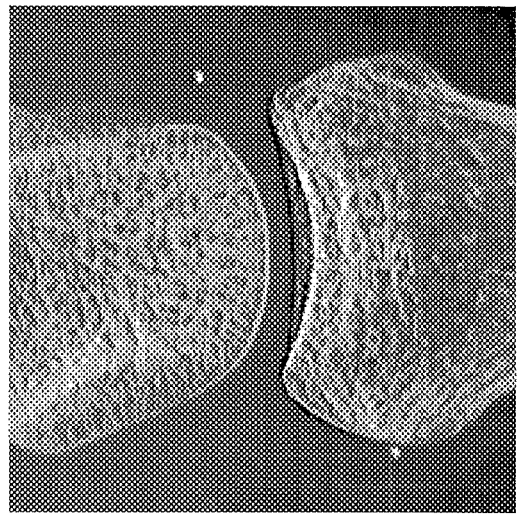
FIG. 9A illustrates a combined image (differential phase image+absorption image) of the absorption image of the wrist joint illustrated in FIG. 7A and the differential phase image of the wrist joint illustrated in FIG. 7B.

FIG. 9A illustrates a combined image (differential phase image+absorption image) of the absorption image of the wrist joint illustrated in FIG. 7A and the differential phase image of the wrist joint illustrated in FIG. 7B.

Figure 9B:
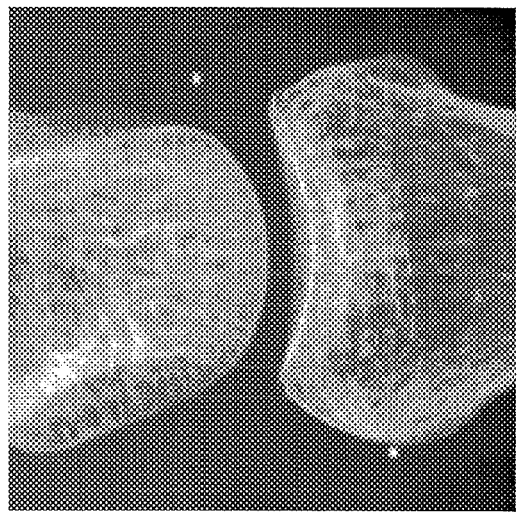
FIG. 9B illustrates a combined image (small-angle scattering image+absorption image) of the absorption image of the wrist joint illustrated in FIG. 7A and the small-angle scattering image of the wrist joint illustrated in FIG. 7C.

FIG. 9B illustrates a combined image (small-angle scattering image+absorption image) of the absorption image of the wrist joint illustrated in FIG. 7A and the small-angle scattering image of the wrist joint illustrated in FIG. 7C.

Figure 9C:
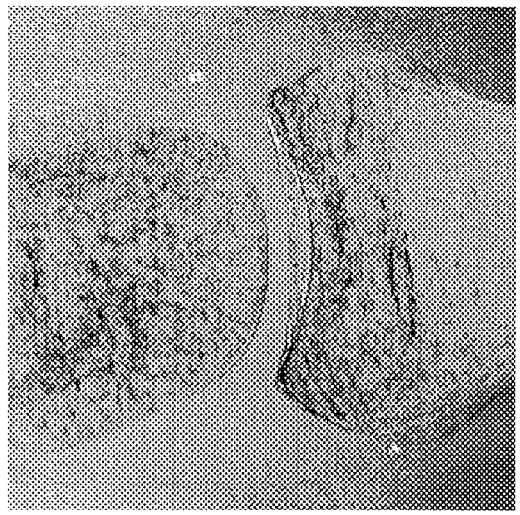
FIG. 9C illustrates a combined image (small-angle scattering image−absorption image) of the absorption image of the wrist joint illustrated in FIG. 7A and the small-angle scattering image of the wrist joint illustrated in FIG. 7C.

FIG. 9C illustrates a combined image (small-angle scattering image–absorption image) of the absorption image of the wrist joint illustrated in FIG. 7A and the small-angle scattering image of the wrist joint illustrated in FIG. 7C.

The value "small-angle scattering image/absorption image" indicates an X-ray dispersion amount in substance defined with an absorption amount. At a certain absorption amount, a higher value indicates a finer trabecula whereas a lower value indicates a larger trabecula. The periodic observations of variations in the ratio at the same site in the same patient can evaluate the progress of osteoporosis. The conversion of the results of the inspection from images into values with an index based on the ratio "small-angle scattering image/absorption image" can significantly reduce data to be stored.

As shown in Table 1, with respect to diagnosis target items (a tumor, a spiculation, and a microcalcification) for the diagnosis of breast cancer, although the absorption image depicts all the tumor, spiculation, and microcalcification, the absorption image alone is insufficient for the diagnosis of a tumor and may lead to oversight of a spiculation or a microcalcification. The differential phase image depicts the structure of a spiculation sufficiently for the diagnosis, but is insufficient for the diagnosis of the other diseases or may lead to oversight. The small-angle scattering image depicts a microcalcification sufficiently for the diagnosis, but is insufficient for the diagnosis of the other diseases or may lead to oversight.

Figure 10A:
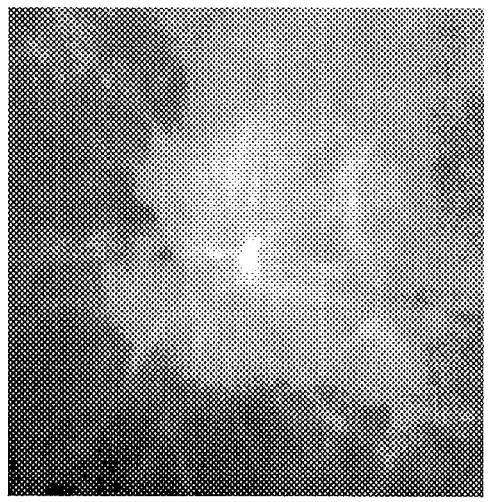
FIG. 10A illustrates an absorption image of a breast as a subject.
Figure 10B:
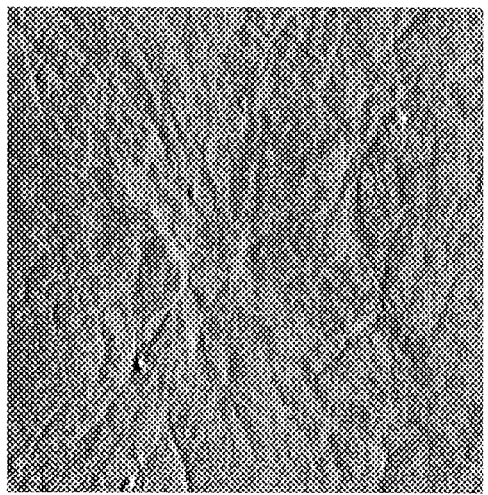
FIG. 10B illustrates a differential phase image of a breast as a subject.
Figure 10C:
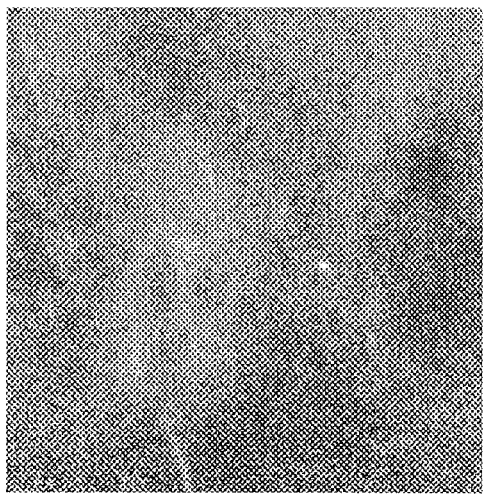
FIG. 10C illustrates a small-angle scattering image of a breast as a subject.

FIG. 10A illustrates an absorption image of a breast as a subject. FIG. 10B illustrates a differential phase image of the breast as a subject. FIG. 10C illustrates a small-angle scattering image of the breast as a subject.

As shown in Table 1, the combined image of the absorption image and the differential phase image clearly depicts the edge of a tumor and the structure of a spiculation. The combined image of the absorption image familiar to medical doctors and the differential phase image is accessible to even medical doctors unfamiliar with the differential phase image and facilitates the medical doctors to diagnose a tumor and inspect the structure of a spiculation.

The combined image of the absorption image and the small-angle scattering image sufficiently depicts the internal structure of a tumor and a faint microcalcification that may escape detection based on the absorption image. The combined image of the absorption image familiar to medical doctors and the small-angle scattering image is accessible to even medical doctors unfamiliar with the small-angle scattering image and facilitates the medical doctors to estimate the internal structure of a tumor and diagnose a microcalcification.

Figure 11A:
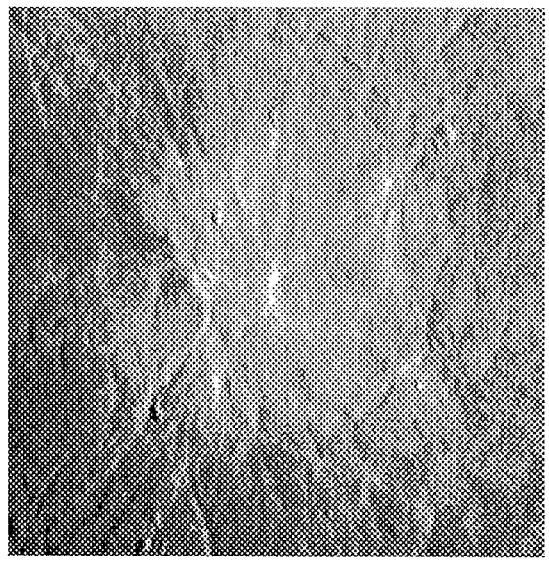
FIG. 11A illustrates a combined image (differential phase image+absorption image) of the absorption image illustrated in FIG. 10A and the differential phase image illustrated in FIG. 10B.
Figure 11B:
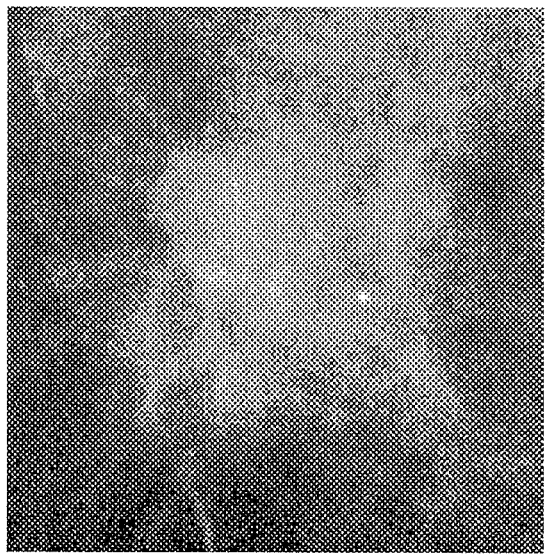
FIG. 11B illustrates a combined image (small-angle scattering image+absorption image) of the absorption image illustrated in FIG. 10A and the small-angle scattering image illustrated in FIG. 10C.

FIG. 11A illustrates a combined image (differential phase image+absorption image) of the absorption image illustrated in FIG. 10A and the differential phase image illustrated in FIG. 10B. FIG. 11B illustrates a combined image (small-angle scattering image+absorption image) of the absorption image illustrated in FIG. 10A and the small-angle scattering image illustrated in FIG. 10C.

The combined image may also be composed of reconstructed images or regions or pixels thereof having different contribution rates, other than the reconstructed images having a ratio of 1:1.

For example, the combined image table may store the type of combined image and the contribution rates of the respective reconstructed images to be combined, in conjunction with the diagnosis target information, to create a combined image based on the contribution rates.

Figure 12A:
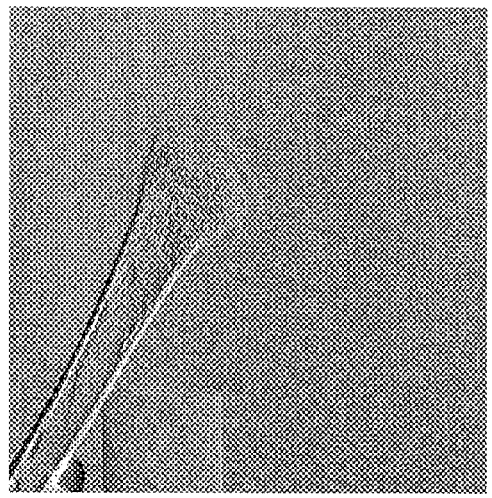
FIG. 12A illustrates an example differential phase image of a fowl wing that has a contribution rate of 1 in the entire region.
Figure 12B:
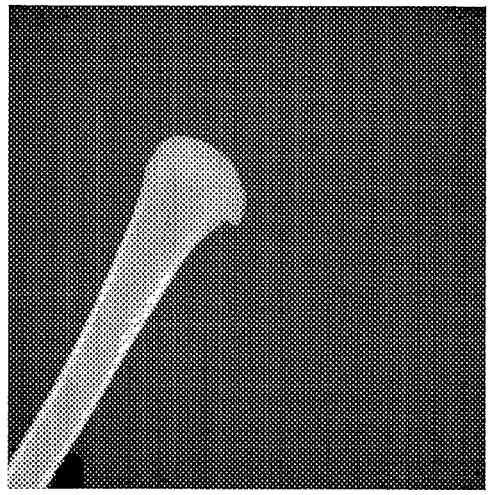
FIG. 12B illustrates an example absorption image of a fowl wing that has a contribution rate of 1 in a bone region and a contribution rate of 0 in the other region.
Figure 12C:
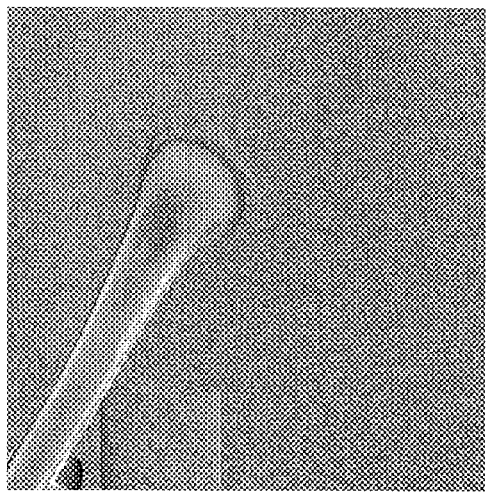
FIG. 12C illustrates an example combined image of the differential phase image illustrated in FIG. 12A and the absorption image illustrated in FIG. 12B, in which the absorption image has a contribution rate of 1 in a bone region whereas the differential phase image has a contribution rate of 1 in the other region.

Alternatively, for example, the combined image table may store the type of combined image, and a region to be extracted from the combined image (e.g., bone or cartilage) and the contribution rates of the respective regions (the extracted region and the non-extracted region) in conjunction with the diagnosis target information, to create a combined image based on the contribution rates. For example, FIG. 12C illustrates a combined image of the differential phase image (having a contribution rate of 1 in the entire region) illustrated in FIG. 12A and the absorption image (having a contribution rate of 1 in a bone region and a contribution rate of 0 in the other region) illustrated in FIG. 12B, in which the absorption image has a contribution rate of 1 in a bone region whereas the differential phase image has a contribution rate of 1 in the other region. The combined image thus contains the absorption image facilitating the diagnosis by medical doctors in the bone region and the differential phase image depicting cartilage in the other region.

Alternatively, for example, the combined image table may store the type of combined image and the contribution rates of the pixels having different image densities in each reconstructed image to be combined, in conjunction with the diagnosis target information, to create a combined image based on the contribution rates. Variations in the contribution rates among the pixels having different image densities can reduce the noise in the combined image, because the noise in an X-ray image depends on the image density (the number of photons detected by the detector).

Alternatively, for example, the combined image table may store the type of combined image and the contribution rate of each pixel defined by differences from the surrounding pixels (the flatness of signals from a subject) in each reconstructed image to be combined, in conjunction with the diagnosis target information, to create a combined image based on the contribution rates. A reduction in the contribution rate of the flat region, which merely adds noise without increasing the contrast of the combined image, can reduce the noise in the combined image.

After the creation of the combined image, an image displaying process is executed based on the diagnosis target information contained in the imaging order information (Step S6). When images are sequentially displayed on the display screen of the displaying unit 23 in the process in Step S6 described below, these images are displayed in the same size in the same region on the display screen of the displaying unit 23, such that the corresponding portions of a subject in the images are displayed in the same region on the screen.

FIG. 13 is a flowchart illustrating the image displaying process executed in Step S6 in the diagnosis in breasts.

The displaying unit 23 displays the combined image of the absorption image and the differential phase image and the combined image of the absorption image and the small-angle scattering image simultaneously (side by side), or alternately (while repeatedly switching between one and the other) (Step T1).

In the diagnosis in breasts, the entire image region is generally inspected for an abnormal shadow candidate, such as a tumor, a spiculation, or a microcalcification. If any abnormal shadow candidate is detected, detailed image interpretation and diagnosis are focused on the region containing the abnormal shadow candidate.

However, none of the reconstructed images alone can depict all the tumor, spiculation, and microcalcification sufficiently for the diagnosis, as shown in Table 1. The combined images of two reconstructed images depict all the tumor, spiculation, and microcalcification, but are each evaluated as "B" for a certain item in Table 1. Inexperienced medical doctors thus may overlook a disease in a combined image alone. Although these kinds of three reconstructed images may be combined, the combined image of the three kinds of reconstructed images, which contains a plurality of pieces of information superimposed, cannot be readily interpreted in the absence of a complicated and sophisticated combining operation.

The study of the present inventors revealed that the simultaneous or alternate display of the combined image of the absorption image and the differential phase image and the combined image of the absorption image and the small-angle scattering image on the displaying unit 23 can streamline the process of inspecting breasts for an abnormal shadow candidate in an early stage of the diagnosis.

Through the comparison of the two combined images in the simultaneous or alternate display, a medical doctor can more readily find an abnormal shadow candidate than through the observation of any one of the combined images alone. In particular, if the two combined images that are alternately displayed one after the other have any difference (e.g., a region displayed in only one image and not the other), the medical doctor can immediately notice the difference. This configuration thus enables rapid and accurate detection of an abnormal shadow candidate, i.e., can facilitate early diagnosis and improve the diagnostic accuracy.

Alternatively, the displaying unit 23 may simultaneously or alternately display either one of the two combined images and the combined image of the three kinds of reconstructed images (absorption image, differential phase image, and small-angle scattering image). The combined image of the three kinds of reconstructed images that can be compared with another combined image rather than being displayed alone allows the medical doctor to readily find a lesion on the basis of a difference (change) between the combined image of the three kinds of reconstructed images and the other combined image.

Alternatively, the displaying unit 23 may simultaneously or alternately display one of the differential phase image and the small-angle scattering image alone in the three kinds of reconstructed images, and the combined image of the other reconstructed image and the absorption image. The images displayed in this mode can sufficiently depict all items for the diagnosis of breast cancer shown in Table 1, although this mode is less compatible with the conventional diagnosis based on an absorption image.

Although the three kinds of reconstructed images may also be simultaneously or sequentially displayed, a human can compare only two images at once and cannot sufficiently compare discontinuous two images in three or more images. To solve this problem, the absorption image should be displayed every other switching cycle, i.e., the images should be displayed in time sequence of the absorption image, the differential phase image, the absorption image, the small-angle scattering image, the absorption image, the differential phase image, and so on, and thereby the above situation is improved.

The combined image of the absorption image and the differential phase image or small-angle scattering image is more compatible with the conventional diagnosis and thus is more accessible to medical doctors, compared to the differential phase image or small-angle scattering image alone. Accordingly, the simultaneous or alternate display of two combined images each containing the absorption image according to the embodiment has higher diagnostic accuracy and thus is superior.

The screen displayed in Step T1 contains the one or two combined images, an operation button for instructing to "inspect the tumor edge or the speculation closely," an operation button for instructing to "inspect the tumor homogeneity or the microcalcification closely," and an operation button for instructing to "end the process." The display in Step T1 allows the medical doctor to generally find the presence of an abnormal shadow candidate in breasts, the type of the abnormal shadow candidate, and the region containing the abnormal shadow candidate. The medical doctor thus can determine a region or object of interest and an item or items to be observed in detail. Through the observation of the display in Step T1, the medical doctor operates any of the operation buttons, and views any individual reconstructed image suitable for the object if necessary.

If any one of the operation buttons is operated through the operating unit 22, whether the operation button to "inspect the tumor edge or the spiculation closely" is operated is determined (Step T2). If the operation button to "inspect the tumor edge or the spiculation closely" is operated (Step T2; Yes), the displaying unit 23 displays the combined image of the absorption image and the differential phase image, and a graphical user interface (GUI) for changing the contribution rates of the differential phase image and the absorption image (the contribution rates of the respective images, regions, or pixels) in response to an operation to the operating unit 22 (Step T3).

The GUI may be a button for discretely changing the contribution rates, or a slider bar for more contentiously changing the contribution rates.

If an instruction to change the contribution rates is input through the operating unit 22 (Step T4; Yes), the contribution rates of the differential phase image and the absorption image are each changed in response to the operation to the operating unit 22, and a combined image is re-created (Step T5). The process then returns to Step T3, and the displaying unit 23 displays the combined image based on the changed contribution rates. The medical doctor changes the contribution rates of the respective reconstructed images through an operation to the slider bar or button to modify the combined image to increase its visibility for the diagnosis. Through the observation of a variation in the combined image caused by the changes in the contribution rates, the medical doctor can determine the intensity of the phase shift relative to the X-ray absorption in the object of interest. The results of the determination may be information for specifying the material of the object of interest.

If the contribution rate of one of the reconstructed images is changed to 0, the other reconstructed image is displayed alone. In other words, the differential phase image or the absorption image can be separately displayed.

If the operation button to "inspect the tumor homogeneity or the microcalcification closely" is operated through the operating unit 22 (Step T2; No, Step T6; Yes), the displaying unit 23 displays the combined image of the absorption image and the small-angle scattering image, and a GUI, such as a button or a slider bar, for changing the contribution rates of the small-angle scattering image and the absorption image (the contribution rates of the respective images, regions, or pixels) in response to an operation to the operating unit 22 (Step T7).

If an instruction to change the contribution rates is input through the operating unit 22 (Step T8; Yes), the contribution rates of the small-angle scattering image and the absorption image are each changed in response to the operation to the operating unit 22, and a combined image is re-created (Step T9). The process then returns to Step T7, and the displaying unit 23 displays the combined image based on the changed contribution rates. The medical doctor changes the contribution rates of the respective reconstructed images through an operation to the slider bar or button to modify the combined image to increase its visibility for the diagnosis. Through the observation of a variation in the combined image caused by the changes in the contribution rates, the medical doctor can determine the intensity of the dispersion of X rays relative to the absorption in the object of interest. The results of the determination may be information for specifying the material of the object of interest.

If the contribution rate of one of the reconstructed images is changed to 0, the other reconstructed image is displayed alone. In other words, the small-angle scattering image or the absorption image can be separately displayed.

The process from Steps T2 to T9 is repeated until the operation button to "end the process" is operated through the operating unit 22. If the operation button to "end the process" is operated through the operating unit 22 (Step T10; Yes), the process goes to Step S7 in FIG. 3.

Figure 14:
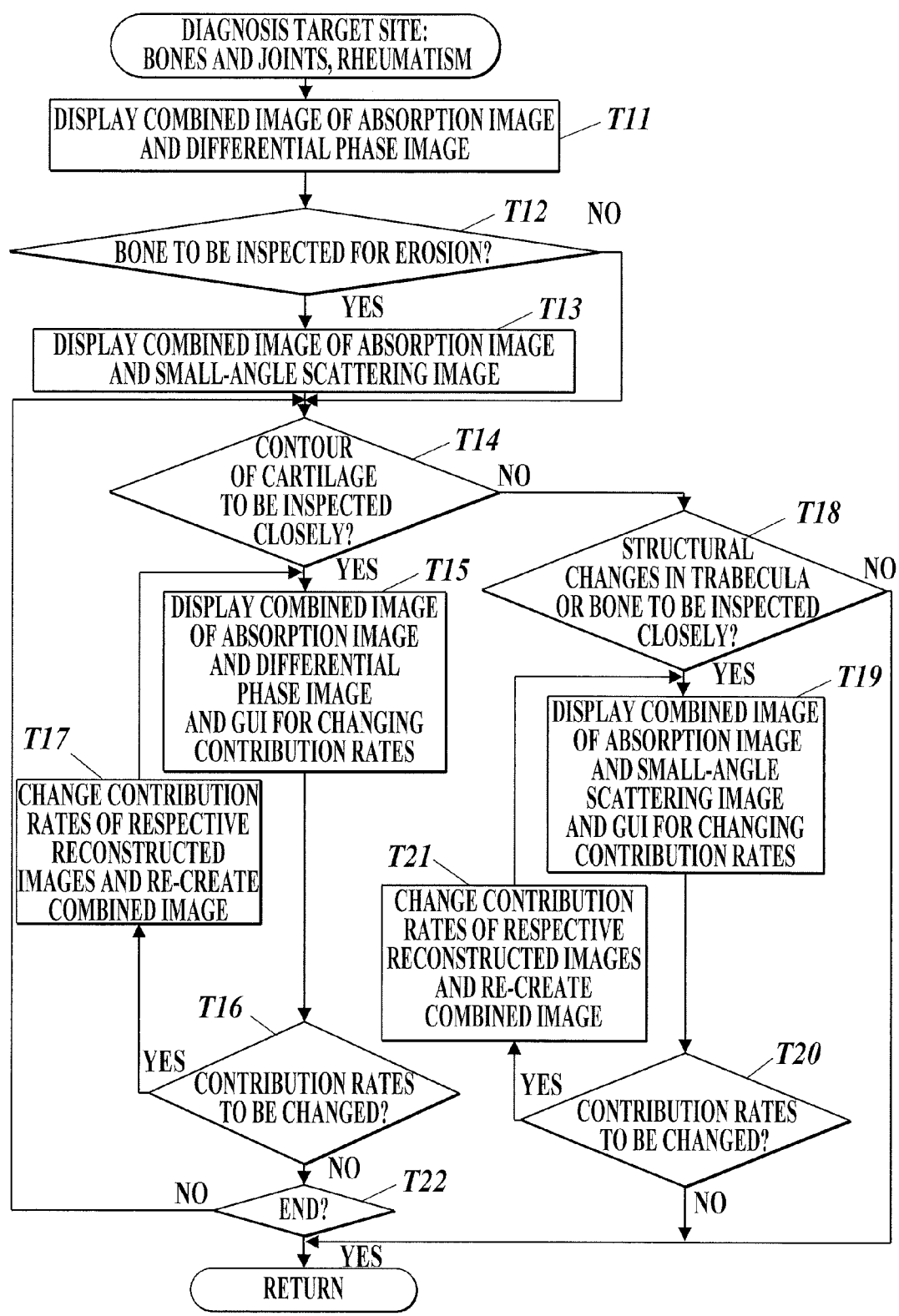
FIG. 14 is a flowchart illustrating an image displaying process executed by the control unit illustrated in FIG. 2 in the diagnosis of rheumatism in bones and joints.

FIG. 14 is a flowchart illustrating an image displaying process executed in Step S6 in the diagnosis of rheumatism in bones and joints.

The displaying unit 23 displays the combined image of the absorption image and the differential phase image (Step T11). Through the observation of the combined image of the absorption image and the differential phase image, a medical doctor can inspect a cartilage for an abnormality and determine a region of interest.

The screen displayed in Step T11 contains the image, an operation button for instructing to "inspect the bone for erosion," an operation button for instructing to "inspect the contour of the cartilage closely," an operation button for instructing to "inspect structural changes in the trabecula or the bone closely", and an operation button for instructing to "end the process." The display in Step T11 allows the medical doctor to inspect the cartilage for an abnormality. The medical doctor operates any of the operation buttons on the basis of the results of the inspection, and views the combined image of the absorption image and the small-angle scattering image or any individual reconstructed image suitable for the object if necessary. It is noted that the operation button for instructing to "inspect the bone for erosion" is inactivated upon a press of any other operation button.

Whether the operation button to "inspect the bone for erosion" is operated through the operating unit 22 is then determined (Step T12). If the operation button to "inspect the bone for erosion" is not operated through the operating unit 22 (Step T12; No), the process goes to Step T14. If the operation button to "inspect the bone for erosion" is operated through the operating unit 22 (Step T12; Yes), the combined image of the absorption image and the small-angle scattering image is displayed (Step T13), and the process goes to Step T14. In general, advanced rheumatism affects a bone under a cartilage. For example, the bone under the cartilage is eroded by granulation tissue in the marrow. The medical doctor can inspect the bone for erosion through the observation of the combined image of the absorption image and the small-angle scattering image, the small-angle scattering image being suitable for the observation of a slight variation in the bone. Alternatively, an image created by combining the combined image displayed in Step T11 and the small-angle scattering image may be displayed in Step T13.

If any one of the operation buttons is operated through the operating unit 22 in Step T14, whether the operation button to "inspect the contour of the cartilage closely" is operated is determined (Step T14). If the operation button to "inspect the contour of the cartilage closely" is operated (Step T14; Yes), the displaying unit 23 displays the combined image of the absorption image and the differential phase image, and a GUI, such as a button or a slider bar, for changing the contribution rates of the differential phase image and the absorption image (the contribution rates of the respective images, regions, or pixels) in response to an operation to the operating unit 22 (Step T15).

If an instruction to change the contribution rates is input through the operating unit 22 (Step T16; Yes), the contribution rates of the differential phase image and the absorption image are each changed in response to the operation to the operating unit 22, and a combined image is re-created (Step T17). The process then returns to Step T15, and the displaying unit 23 displays the combined image based on the changed contribution rates. The medical doctor changes the contribution rates of the respective reconstructed images through an operation to the slider bar or button to modify the combined image to increase its visibility for the diagnosis. Through the observation of a variation in the combined image caused by the changes in the contribution rates, the medical doctor can specify the material represented by a certain signal component in the region of interest. For example, a cartilage is depicted in the differential phase image but not in the absorption image. In the region of interest containing a cartilage overlying a bone, the cartilage is represented by the signal component that gradually disappears as the contribution rate of the differential phase image approaches 0.

If the contribution rate of one of the reconstructed images is changed to 0, the other reconstructed image is displayed alone. In other words, the differential phase image or the absorption image can be separately displayed.

If the operation button to "inspect structural changes in the trabecula or the bone closely" is operated through the operating unit 22 (Step T14; No, Step T18; Yes), the displaying unit 23 displays the combined image of the absorption image and the small-angle scattering image, and a GUI, such as a button or a slider bar, for changing the contribution rates of the small-angle scattering image and the absorption image (the contribution rates of the respective images, regions, or pixels) in response to an operation to the operating unit 22 (Step T19).

If an instruction to change the contribution rates is input through the operating unit 22 (Step T20; Yes), the contribution rates of the small-angle scattering image and the absorption image are each changed in response to the operation to the operating unit 22, and a combined image is re-created (Step T21). The process then returns to Step T19, and the displaying unit 23 displays the combined image based on the changed contribution rates. The medical doctor can change the contribution rates of the respective reconstructed images through an operation to the slider bar or button to modify the combined image to increase its visibility for the diagnosis. Through the observation of a variation in the combined image caused by the changes in the contribution rates, the medical doctor can determine the intensity of the dispersion of X rays relative to the absorption in the object of interest. The results of the determination contribute to the estimation of the size, orientation, and shape of the trabecular fine structures. If the contribution rate of one of the reconstructed images is changed to 0, the other reconstructed image is displayed alone. In other words, the small-angle scattering image or the absorption image can be separately displayed.

The process from Steps T14 to T21 is repeated until the operation button to "end the process" is operated through the operating unit 22. If the operation button to "end the process" is operated through the operating unit 22 (Step T22; Yes), the process goes to Step S7 in FIG. 3.

Figure 15:
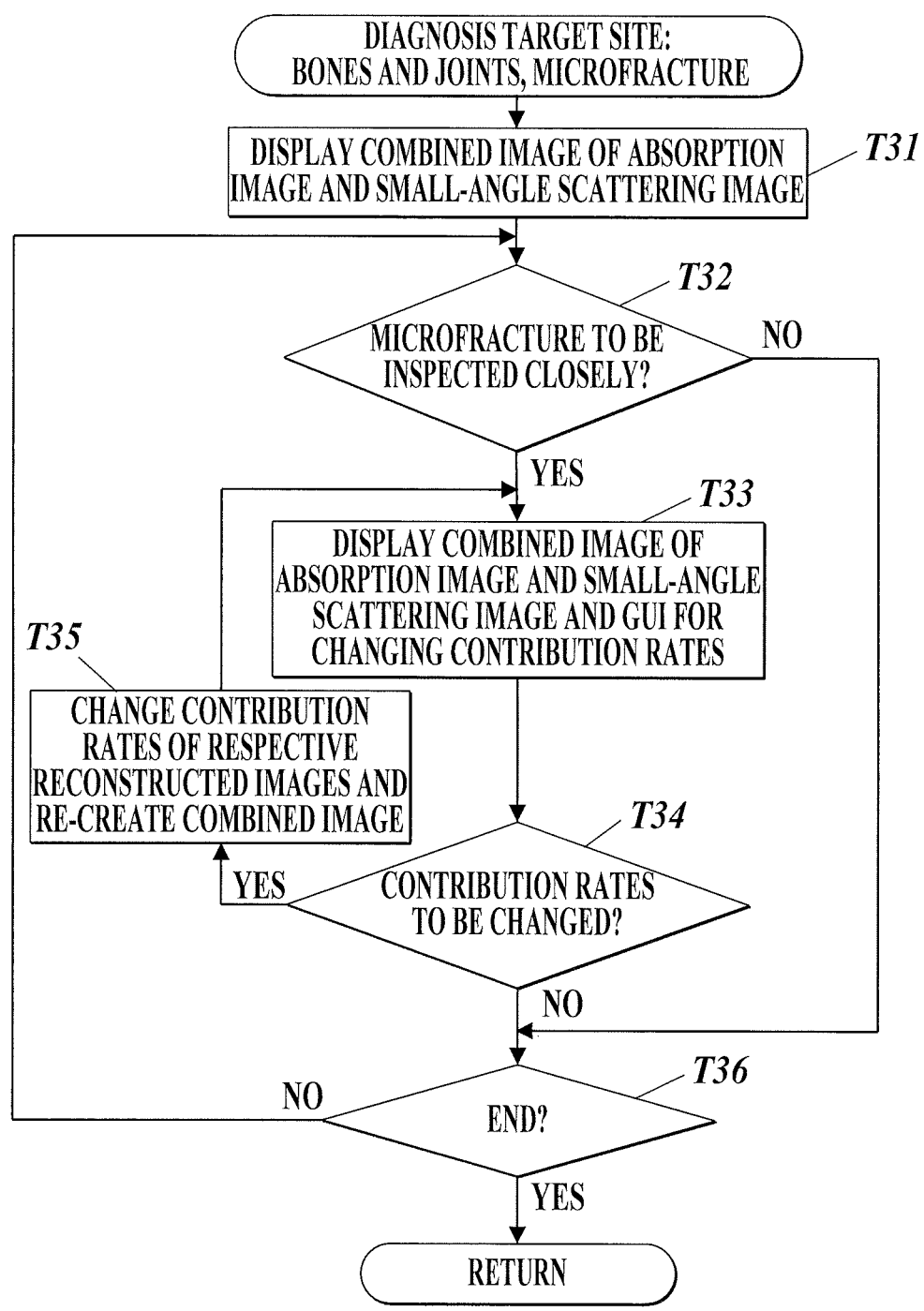
FIG. 15 is a flowchart illustrating an image displaying process executed by the control unit illustrated in FIG. 2 in the diagnosis of a microfracture in bones and joints.

FIG. 15 is a flowchart illustrating an image displaying process executed in Step S6 in the diagnosis of a microfracture in bones and joints.

The displaying unit 23 displays the combined image of the absorption image and the small-angle scattering image (Step T31). Through the observation of the combined image of the absorption image and the small-angle scattering image, a medical doctor can inspect a bone for a microfracture or a fracture and determine a region of interest.

The screen displayed in Step T31 displays the combined image, an operation button for instructing to "inspect the microfracture closely", and an operation button for instructing to "end the process".

If the operation button to "inspect the microfracture closely" is operated through the operating unit 22 (Step T32; Yes), the displaying unit 23 displays the combined image of the absorption image and the small-angle scattering image, and a GUI, such as a button or a slider bar, for changing the contribution rates of the small-angle scattering image and the absorption image (the contribution rates of the respective images, regions, or pixels) in response to an operation to the operating unit 22 (Step T33).

If an instruction to change the contribution rates is input through the operating unit 22 (Step T34; Yes), the contribution rates of the small-angle scattering image and the absorption image are each changed in response to the operation to the operating unit 22, and a combined image is re-created (Step T35). The process then returns to Step T33, and the displaying unit 23 displays the combined image based on the changed contribution rates.

The medical doctor can change the contribution rates of the respective reconstructed images through an operation to the slider bar or button to modify the combined image to increase its visibility for the diagnosis. Through the observation of a variation in the combined image caused by the changes in the contribution rates, the medical doctor can determine the intensity of the dispersion of X rays relative to the absorption in the object of interest. The results of the determination contribute to the estimation of the size, orientation, and shape of the microfracture. If the contribution rate of one of the reconstructed images is changed to 0, the other reconstructed image is displayed alone. In other words, the small-angle scattering image or the absorption image can be separately displayed.

The process from Steps T32 to T35 is repeated until the operation button to "end the process" is operated through the operating unit 22. If the operation button to "end the process" is operated through the operating unit 22 (Step T36; Yes), the process goes to Step S7 in FIG. 3.

Although only the combined images are displayed in the example image displaying process in Step S6 in FIG. 3 as explained above, the combined images have both advantages and disadvantages.

Examples of the advantages include: (1) a single combined image can depict a number of elements and thus enables more efficient diagnosis than that based on the comparison of individual reconstructed images; (2) a combined image of an absorption image and a differential phase image or small-angle scattering image is compatible with the conventional diagnosis; and (3) a combined image can depict an object of interest with higher visibility if the increase in noise caused by the combining operation is smaller than the increase in signals representing the object.

Examples of the disadvantages include that the performance of the diagnosis based on a combined image is lower than that based on an individual reconstructed image if the increase in noise is larger than the increase in signals representing the object of interest. This disadvantage can be reduced through changes in the contribution rates of the respective reconstructed images depending on the image densities or the flatness of signals, as described above. In the processes illustrated in FIGS. 13 to 15, any one of the individual reconstructed images constituting the combined image can be displayed through the adjustment of the contribution rates of the respective reconstructed images. This configuration enables the display of an individual reconstructed image free from the disadvantages of the combined image. Alternatively, the display of a combined image may be switched to the display of an individual reconstructed image suitable for the object determined through the observation of the combined image. This configuration enables an individual reconstructed image to be displayed free from the disadvantages of the combined image without the adjustment of the contribution rates.

Another example image displaying process in Step S6 in FIG. 3 will now be explained. This process includes the display of a combined image and then switching to the display of individual reconstructed images.

Figure 16:
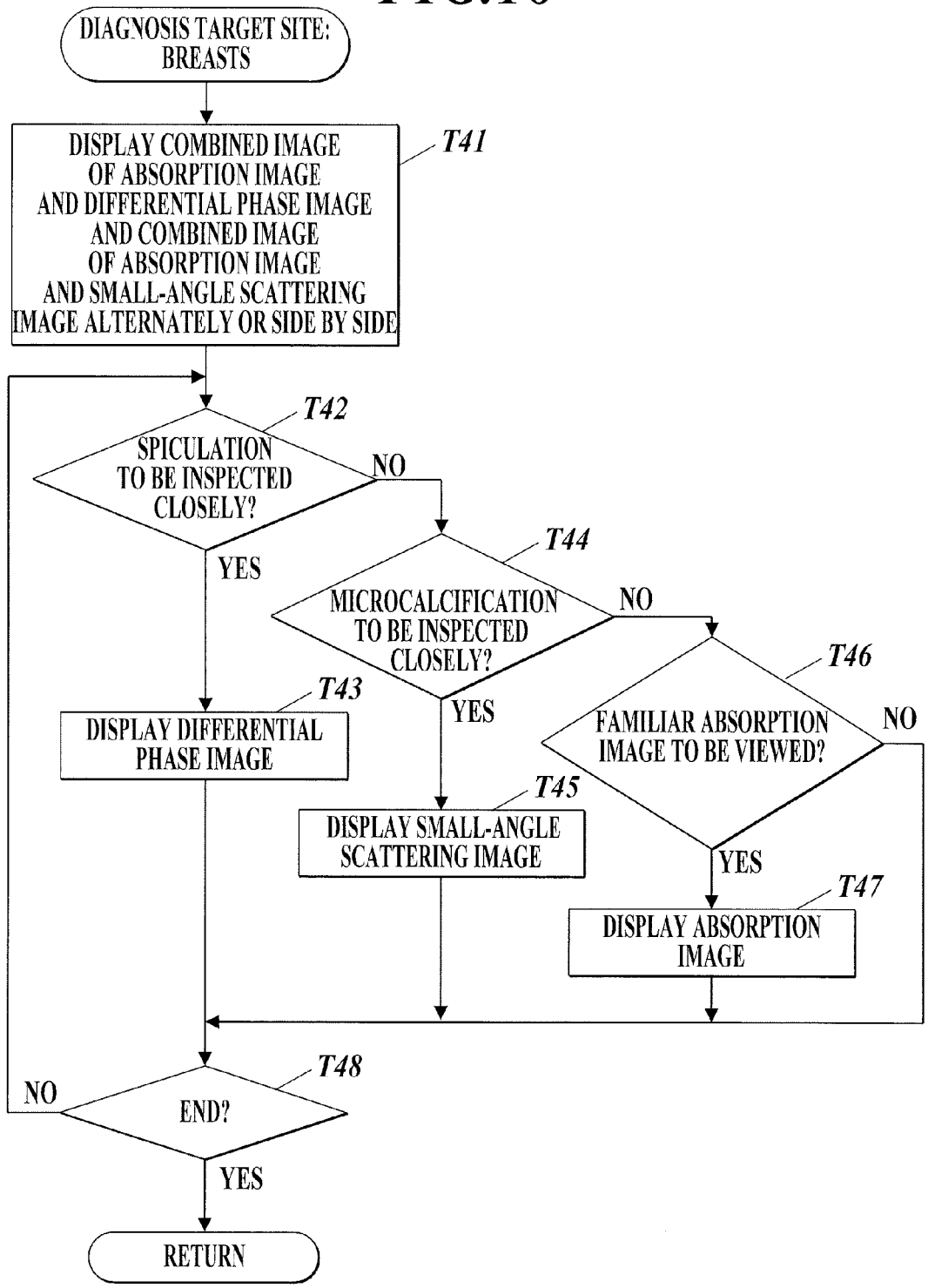
FIG. 16 is a flowchart illustrating another example image displaying process executed by the control unit illustrated in FIG. 2 in the diagnosis in breasts.

FIG. 16 is a flowchart illustrating another example image displaying process executed in Step S6 in FIG. 3 in the diagnosis in breasts.

The displaying unit 23 displays the combined image of the absorption image and the differential phase image and the combined image of the absorption image and the small-angle scattering image simultaneously (side by side), or alternately (while repeatedly switching between one and the other) (Step T41).

The screen displayed in Step T41 contains the one or two combined images, an operation button for instructing to "inspect the speculation closely", an operation button for instructing to "inspect the microcalcification closely" an operation button for instructing to "view a familiar absorption image," and an operation button for instructing to "end the process." The display in Step T41 allows a medical doctor to generally find the presence of an abnormal shadow candidate in breasts, the type of the abnormal shadow candidate, and the region containing the abnormal shadow candidate. The medical doctor thus can determine a region of interest and an item or items to be observed in detail. Through the observation of the display in Step T41, the medical doctor operates any of the operation buttons, and views any individual reconstructed image suitable for the object if necessary.

If any one of the operation buttons is operated through the operating unit 22, whether the operation button to "inspect the speculation closely" is operated is determined (Step T42). If the operation button to "inspect the speculation closely" is operated (Step T42; Yes), the displaying unit 23 displays the differential phase image (Step T43).

If the operation button to "inspect the microcalcification closely" is operated through the operating unit 22 (Step T42; No, Step T44; Yes), the displaying unit 23 displays the small-angle scattering image (Step T45).

If the operation button to "view a familiar absorption image" is operated through the operating unit 22 (Step T44; No, Step T46; Yes), the displaying unit 23 displays the absorption image (Step T47).

The process from Steps T42 to T47 is repeated until the operation button to "end the process" is operated through the operating unit 22. If the operation button to "end the process" is operated through the operating unit 22 (Step T48; Yes), the process goes to Step S7 in FIG. 3.

Figure 17:
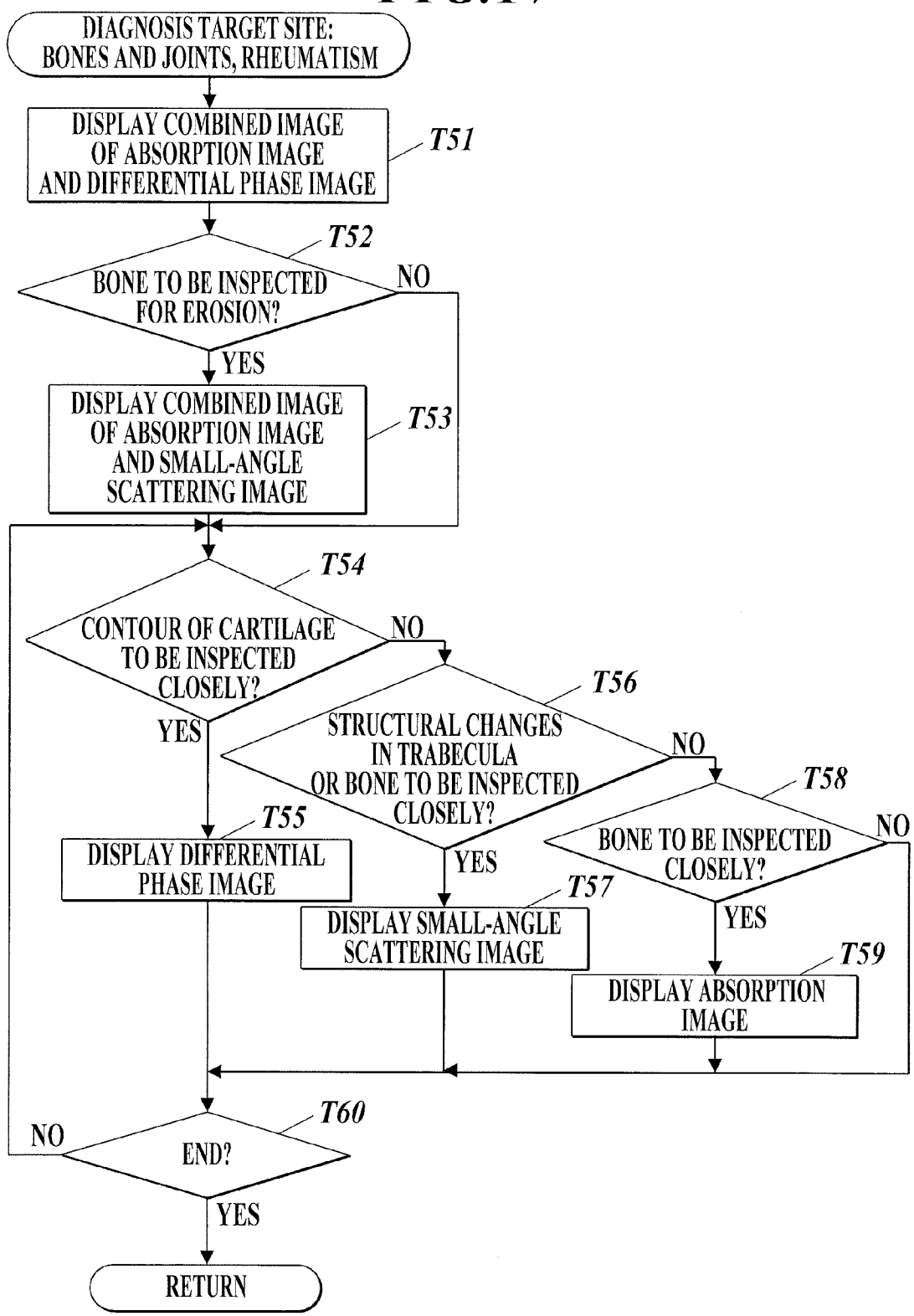
FIG. 17 is a flowchart illustrating another example image displaying process executed by the control unit illustrated in FIG. 2 in the diagnosis of rheumatism in bones and joints.

FIG. 17 is a flowchart illustrating another example image displaying process executed in Step S6 in the diagnosis of rheumatism in bones and joints.

First, the displaying unit 23 displays the combined image of the absorption image and the differential phase image (Step T51). Through the observation of the combined image of the absorption image and the differential phase image, a medical doctor can inspect a cartilage for an abnormality and determine a region of interest.

The screen displayed in Step T51 contains the combined image, an operation button for instructing to "inspect the bone for erosion," an operation button for instructing to "inspect the contour of the cartilage closely", an operation button for instructing to "inspect structural changes in the trabecula or the bone closely", an operation button for instructing to "inspect the bone closely", and an operation button for instructing to "end the process". The display in Step T51 allows the medical doctor to inspect the cartilage for an abnormality. The medical doctor operates any of the operation buttons on the basis of the results of the inspection, and views the combined image of the absorption image and the small-angle scattering image or any individual reconstructed image suitable for the object if necessary. It is noted that the operation button for instructing to "inspect the bone for erosion" is inactivated upon a press of any other operation button.

Whether the operation button to "inspect the bone for erosion" is operated through the operating unit 22 is then determined (Step T52). If the operation button to "inspect the bone for erosion" is not operated through the operating unit 22 (Step T52; No), the process goes to Step T54. If the operation button to "inspect the bone for erosion" is operated through the operating unit 22 (Step T52; Yes), the combined image of the absorption image and the small-angle scattering image is displayed (Step T53), and the process goes to Step T54. Alternatively, an image created by combining the combined image displayed in Step T51 and the small-angle scattering image may be displayed in Step T53.

If any one of the operation buttons is operated through the operating unit 22 in Step T54, whether the operation button to "inspect the contour of the cartilage closely" is operated is determined (Step T54). If the operation button to "inspect the contour of the cartilage closely" is operated (Step T54; Yes), the displaying unit 23 displays the differential phase image (Step T55).

If the operation button to "inspect structural changes in the trabecula or the bone closely" is operated through the operating unit 22 (Step T54; No, Step T56; Yes), the displaying unit 23 displays the small-angle scattering image (Step T57).

If the operation button to "inspect the bone closely" is operated through the operating unit 22 (Step T56; No, Step T58; Yes), the displaying unit 23 displays the absorption image (Step T59).

The process from Steps T54 to T59 is repeated until the operation button to "end the process" is operated through the operating unit 22. If the operation button to "end the process" is operated through the operating unit 22 (Step T60; Yes), the process goes to Step S7 in FIG. 3.

Figure 18:
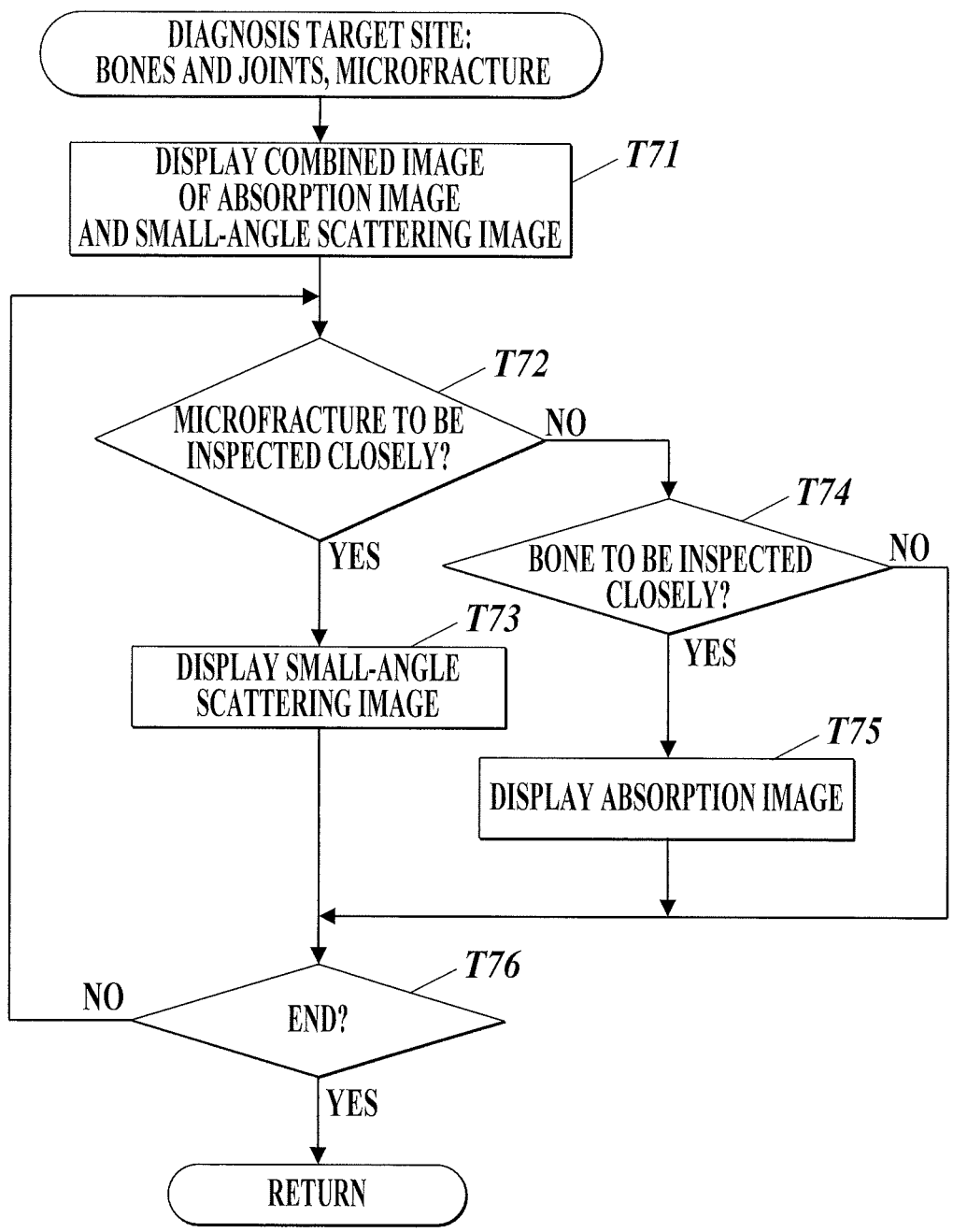
FIG. 18 is a flowchart illustrating another example image displaying process executed by the control unit illustrated in FIG. 2 in the diagnosis of a microfracture in bones and joints.

FIG. 18 is a flowchart illustrating another example image displaying process executed in Step S6 in the diagnosis of a microfracture in bones and joints.

The displaying unit 23 displays the combined image of the absorption image and the small-angle scattering image (Step T71). Through the observation of the combined image of the absorption image and the small-angle scattering image, a medical doctor can inspect a bone for a microfracture or a fracture and determine a region of interest.

The screen displayed in Step T71 contains the combined image, an operation button for instructing to "inspect the microfracture closely", an operation button for instructing to "inspect the bone closely", and an operation button for instructing to "end the process."

If the operation button to "inspect the microfracture closely" is operated through the operating unit 22 (Step T72; Yes), the displaying unit 23 displays the small-angle scattering image (Step T73).

If the operation button to "inspect the bone closely" is operated through the operating unit 22 (Step T72; No, Step T74; Yes), the displaying unit 23 displays the absorption image (Step T75).

The process from Steps T72 to T75 is repeated until the operation button to "end the process" is operated through the operating unit 22. If the operation button to "end the process" is operated through the operating unit 22 (Step T76; Yes), the process goes to Step S7 in FIG. 3.

In Step S7 in FIG. 3, the resulting reconstructed images and combined images, information on the type of the image processing used for the creation of the combined images, image processing parameters, and display parameters are stored in the storage unit 25 in conjunction with the imaging order information designated in Step S1 (Step S7). The combined images can thus be readily read from the storage unit 25 to be displayed again under the same processing conditions if desired. This configuration can improve the usability.

In the example processes in FIGS. 13 to 18, the screen contains the operation buttons (e.g., the operation button for instructing to "inspect the tumor edge or the spiculation closely" and the operation button for instructing to "inspect the tumor homogeneity or the microcalcification closely" displayed in Step T1 in FIG. 13) for displaying a combined image or an individual reconstructed image suitable for the purpose, and is switched to the display of another image in response to an operation to any of the operation buttons. Any other motivation (purpose) or operation may also cause the display of a combined image or an individual reconstructed image.

The differential phase image has a differential value that can be either positive or negative depending on a subject, and appears to human eyes differently depending on the density of the background because of the visual features of the human eyes. The displaying unit 23 may also display an interface for switching the differential value to the differential value having the opposite sign or the absolute differential value, to allow a medical doctor to view an image more suitable for the diagnosis through an operation to the operating unit 22.

As described above, in the medical imaging system 100, the control unit 21 of the controller 2 creates a combined image of two of the three kinds of reconstructed images (absorption image, differential phase image, and small-angle scattering image) on the basis of the diagnosis target information (for specifying a diagnosis target site and/or a disease to be diagnosed in the site) contained in the imaging order information designated through the operating unit 22, and controls the displaying unit 23 to display the combined image.

Depending on the target site and the disease to be inspected, the displayed combined image has rich information effective for the diagnosis compared to individual reconstructed images. This configuration can streamline the diagnosis and improve the diagnostic accuracy.

One of the two reconstructed images to be combined should preferably be an absorption image, which has been used by medical doctors for the conventional diagnosis and is highly compatible with the conventional diagnosis.

In a preferred display mode, for example, two or more types of combined images should preferably be created and simultaneously or alternately displayed on the displaying unit 23.

In specific, in the diagnosis in breasts, the combined image of the absorption image and the differential phase image and the combined image of the absorption image and the small-angle scattering image should preferably be created and simultaneously or alternately displayed on the displaying unit 23. This configuration enables a medical doctor to compare the two combined images. On the basis of the difference between the combined images, the medical doctor can more readily find an abnormal shadow candidate than through the observation of either one of the combined images. In particular, if the two combined images that are alternately displayed one after the other have any difference, the medical doctor can immediately notice the difference. This configuration enables rapid and accurate detection of an abnormal shadow candidate and thus is advantageous.

Alternatively, the displaying unit 23 may simultaneously or alternately display the resulting combined image and at least one of the three kinds of reconstructed images. For example, in the diagnosis in breasts, the displaying unit 23 may simultaneously or alternately display one of the differential phase image and the small-angle scattering image alone in the three kinds of reconstructed images, and the combined image of the other reconstructed image and the absorption image.

Alternatively, the displaying unit 23 may simultaneously or alternately display the combined image of the two kinds of reconstructed images and the combined image of the three kinds of reconstructed images.

The absorption image may be replaced with the differential absorption image created through the differentiation of the absorption image, or an image based on the absolute value of the differential absorption image. The differential phase image may be replaced with an image based on the absolute value of the differential phase image, or a phase image created through the integration of the image based on the absolute value. The small-angle scattering image may be replaced with a differential small-angle scattering image created through the differentiation of the small-angle scattering image, or an image based on the absolute value of the differential small-angle scattering image.

[Second Embodiment]

The second embodiment of the invention will now be described.

The absorption image can depict structures such as a bone with high sensitivity, as described above. The differential phase image can depict a bone and soft tissue, such as a cartilage, that is not readily depicted by the absorption image. However, in a conventional differential phase image that depicts soft tissue (cartilage) overlapping with a bone, it is difficult to visually recognize signals representing the soft tissue that are lower in level than the signals representing the bone.

For example, in a differential phase image acquired by capturing a finger as it is, soft tissue readily overlaps with a bone. To solve this problem in a conventional technique, the imaging angle is adjusted such that the bones of the finger have spaces at the joints in the image. However, this procedure may fail to prevent soft tissue from overlapping with the bone in some individuals having uniquely-shaped fingers.

The study of the inventors revealed that a visible image depicting soft tissue such as cartilage can be created through the removal or attenuation of the signals representing a bone from or in a differential phase image, with an absorption image acquired together with the differential phase image, regardless of the overlap of the soft tissue with the bone. The outline will now be described.

An absorption image $I_{Abs}$ is represented by an integrated value of the physical quantity in the direction of propagating X rays (z direction in FIG. 1B), whereas a differential phase image $dI_{DP}$ is proportional to a differentiated value of the integrated value of the physical quantity in the direction of propagating X rays with respect to the direction perpendicular to the lattice structure (x direction in FIG. 1B), as shown below:

$$I_{Abs} \equiv -\ln(I_{Abs\_RAW}) = \int \mu \cdot dz + C \quad \text{[Expression 1]}$$

$$dI_{DP} \propto \frac{\partial}{\partial x} \int (1-\delta) \cdot dz \quad \text{[Expression 2]}$$

where $I_{Abs}$ indicates the absorption image, $dI_{DP}$ indicates the differential phase image, $I_{Abs\_RAW}$ indicates the (non-logarithmic) intensity of X rays in the absorption image reconstructed with a Talbot or Talbot-Lau interferometer, μ indicates an X-ray absorption coefficient of a subject, and 1-δ indicates an X-ray refractive index of the subject. The relationship between μ and δ varies depending on the subject. Accordingly, the differentiated absorption image $I_{Abs}$ is not equal to the differential phase image $dI_{DP}$, whereas the integrated differential phase image $dI_{DP}$ is not equal to the absorption image $I_{Abs}$. For example, the absorption image $I_{Abs}$ and its differential image can depict a bone but not soft tissue such as cartilage, whereas the differential phase image $dI_{DP}$ and its integral image can depict both the bone and the soft tissue. If the absorption image $I_{Abs}$ and the differential phase image $dI_{DP}$ depict the same structure, an image that depicts only the structures other than the same structure can be created through the subtraction after the adjustment of the intensities of the signals representing the same structure between the images. In other words, an image that depicts soft tissue visibly can be created with the absorption image $I_{Abs}$ and the differential phase image $dI_{DP}$, regardless of the overlap of the soft tissue with a bone in the differential phase image $dI_{DP}$.

A combined image of an absorption image and a differential phase image after the removal or the attenuation of the signals representing a structure common to both images can be created through: (A) the technique of creating a differential absorption image through the processing (differentiation) of the absorption image, multiplying the differential absorption image by a factor for adjusting the intensity of signals representing a structure in the differential absorption image to that in the differential phase image, the structure being common to the differential phase image and the differential absorption image, and subtracting the differential absorption image multiplied by the factor from the differential phase image; or (B) the technique of creating a phase image through the processing (integration) of the differential phase image, multiplying the absorption image by a factor for adjusting the intensity of signals representing a structure in the absorption image to that in the phase image, the structure being common to the phase image and the absorption image, and subtracting the absorption image multiplied by the factor from the phase image. An image that depicts soft tissue with visibility increased through the technique (A) of removing or attenuating the signals representing a bone is referred to as "differential soft-tissue image." An image that depicts soft tissue with visibility increased through the technique (B) of removing or attenuating the signals representing a bone is referred to as "soft-tissue image."

According to the second embodiment, the differential soft-tissue image, which is a combined image of the absorption image and the differential phase image, is created and displayed in the diagnosis of rheumatism in bones and joints.

According to the second embodiment, the combined image table in the storage unit 25 illustrated in FIG. 2 further stores the differential soft-tissue image, which is the combined image to be created in the diagnosis of rheumatism in bones and joints. The storage unit 25 also stores programs (e.g., a program for executing the process of creating a differential soft-tissue image illustrated in FIG. 19) for allowing the control unit 21 to execute the operation according to the second embodiment.

The other configurations of the medical imaging system and the respective apparatuses therein are the same as those of the medical imaging system 100 and the respective apparatuses therein according to the first embodiment, and the description thereof is incorporated herein by reference. The operations of the medical imaging system 100 according to the second embodiment will now be explained.

According to the second embodiment, the control unit 21 of the controller 2 executes the image creating and displaying process illustrated in FIG. 3 in response to an operation to the operating unit 22. In Step S5 according to the second embodiment, a differential soft-tissue image is created by combining a differential absorption image derived from the absorption image with the differential phase image through the process of creating a differential soft-tissue image (explained below), instead of the creation of the combined image of the absorption image and the differential phase image.

FIG. 19 illustrates the process of creating a differential soft-tissue image executed by the control unit 21 of the controller 2.

In the process of creating a differential soft-tissue image, the absorption image and the differential phase image created in Step S4 are acquired (Step S501).

A differential absorption image is then created from the absorption image (Step S502).

The differential absorption image can be created through the differentiation of the absorption image. According to this embodiment, for example, the differential absorption image should preferably be created by taking the difference between two adjacent pixels of the absorption image in the direction (x direction in FIG. 1B) perpendicular to the lattice structure, as shown in Expression 3.

$$dI(x,y)=I(x+1,y)-I(x-1,y) \quad \text{[Expression 3]}$$

dI(x,y): Differential value of pixel (x,y) in x direction
I(x+1,y): Pixel value of pixel (x+1,y)
I(x−1,y): Pixel value of pixel (x−1,y)

Alternatively, the differential absorption image may be created by simply taking the difference between two adjacent pixels of the absorption image, or applying a differential filter, such as a Sobel filter for the detection of the edge of an image, to the absorption image. Alternatively, a differential filter that achieves a differential absorption image having a signal form most correlated with that of the differential phase image may be designed in advance for a simple subject, such as a cylinder or a sphere, to be maintained and applied to the absorption image. Although the absorption image is used in this case, a non-logarithmic absorption image corresponding to $I_{Abs\_RAW}$ in Expression 1 may also be used.

The differential absorption image is then multiplied by a factor for adjusting the intensity of signals representing a certain structure (bone, here) in the differential absorption image to that in the differential phase image, the certain structure being to be removed from the differential phase image among anatomical structures common to the differential phase image and the differential absorption image (Step S503). In specific, the pixel values of the respective pixels of the differential absorption image are multiplied by the factor for adjusting the intensity of the signals representing a bone to that in the differential phase image. The factor may be determined in advance based on the configuration of the apparatus and/or the imaging conditions, or may be calculated before every multiplication. In the latter case, the factor that can achieve the smallest signals representing the same structure (bone) after the subtraction of the differential absorption image from the differential phase image, is calculated. For example, the factor may be the ratio (the signals representing the bone in the differential phase image/the signals representing the bone in the differential absorption image) of the signals representing the same structure (bone, here), to be subtracted and removed from the differential phase image, in the differential phase image to those in the differential absorption image. For example, in a region of interest set as the entire region or the region of a bone, the factor may be the ratio of the pixel values (e.g., the ratio of the representative values of the pixel values) in the region of interest between the two images.

Finally, the differential absorption image multiplied by the factor is then subtracted from the differential phase image, to create a differential phase image (differential soft-tissue image) in which the signals representing the same structure (bone) are removed or attenuated (Step S504). In other words, the pixel values of the respective pixels of the differential absorption image multiplied by the factor are subtracted from the pixel values of the corresponding pixels of the differential phase image, to create a differential phase image (differential soft-tissue image) in which the signals representing the same structure (bone) are removed or attenuated.

Through the process of creating a differential soft-tissue image, a visible differential image depicting soft tissue can be created regardless of the overlap of the soft tissue with a bone in the image.

The positions of the lattices may be slightly shifted between the imaging with a subject and the imaging without the subject because of the temperature or heat in the X-ray imaging apparatus 1. The slight shifts of the lattices barely affect the absorption image, but cause artifacts such as the tilt of signals in the plane of the differential phase image. In such a case, the calculation may fail to yield an appropriate factor that the differential absorption image is multiplied by. The artifacts in the differential phase image caused by the shifts of the lattices can be approximated by a linear or quadratic function in the two-dimensional coordinates (x,y) in the image. Through the estimation and subtraction of a coefficient of the function that best represents the artifact component from the differential phase image, the signals representing the artifact component can be corrected, for example, as is disclosed in Known Literature 6 (Japanese Patent Application No. 2011-035593). Accordingly, the control unit 21 should preferably correct the artifacts in the differential phase image and create a differential soft-tissue image with the corrected differential phase image and the absorption image after the acquisition of the differential phase image in Step S501. Alternatively, the unevenness of signals due to a cause other than the subject may be eliminated from the distribution of signals in the differential phase image and the differential absorption image, to create a differential soft-tissue image.

In the process of creating a differential soft-tissue image illustrated in FIG. 19, the differential absorption image multiplied by a certain factor is subtracted from the differential phase image. For example, the differential phase image of a joint in a region without the overlap of soft tissue with a bone depicts sufficient signals representing the soft tissue. The subtraction of the differential absorption image from this region may increase the noise component and lead to degradation of the image quality. The factor that the differential absorption image is multiplied by should thus preferably be reduced in the region other than a bone region in the differential absorption image. This control can prevent the degradation of the image quality.

In order to specify a bone region, the storage unit 25 stores a threshold corresponding to the absorption image in advance, and the respective pixel values of the absorption image are compared with the threshold. A region satisfying the inequality below is specified to be the bone region:

$$\text{Pixel value of the absorption image} > \text{threshold} \quad (1)$$

It is noted that the threshold is the upper limit of the pixel values in the region other than the bone region because of the definition of the absorption image in Expression 1 (i.e., a region subjected to higher absorption by a subject has a larger pixel value). If a region subjected to a lower absorption by a subject has a larger pixel value, the storage unit 25 stores the lower limit of the pixel values of the region other than the bone region, and a region having pixel values exceeding (smaller) than the lower limit is specified to be the bone region.

Alternatively, the storage unit 25 may store a threshold corresponding to the differential absorption image in advance, and the respective absolute pixel values of the differential absorption image may be compared with the threshold stored in the storage unit 25. A region satisfying the inequality below is specified to be the bone region:

$$\text{Absolute pixel value of the differential absorption image} > \text{threshold} \quad (2)$$

Alternatively, the storage unit 25 may store a threshold corresponding to the small-angle scattering image, and the respective pixel values of the small-angle scattering image may be compared with the threshold, to specify a region satisfying the inequality "(pixel value of the small-angle scattering image)>threshold" as the bone region. Alternatively, the storage unit 25 may store a threshold corresponding to the phase image (described in detail below), and the respective pixel values of the phase image may be compared with the threshold, to specify a region satisfying the inequality "(pixel value of the phase image)>threshold" as the bone region. Alternatively, the storage unit 25 may store a threshold corresponding to the differential phase image, and the respective absolute pixel values of the differential phase image may be compared with the threshold stored in the storage unit 25, to determine a region satisfying the inequality "(absolute pixel value of the differential phase image)>threshold" to be the bone region.

After the process of creating a differential soft-tissue image, the control unit 21 executes the image displaying process in Step S6 in FIG. 3. The image displaying process (FIG. 14) in the diagnosis of rheumatism in bones and joints according to the second embodiment is different from that according to the first embodiment. In specific, in Step T15 in FIG. 14, the displaying unit 23 displays the resulting differential soft-tissue image, which is the combined image of the absorption image and the differential phase image.

The differential soft-tissue image is created through the removal or attenuation of the signals representing a bone from or in the differential phase image that depicts the signals representing the bone and soft tissue (cartilage), as described above. The differential soft-tissue image thus allows a medical doctor to view the signals representing the soft tissue, regardless of the overlap of the soft tissue with the bone.

The screen in Step T15 also contains a GUI, such as a button or a slider bar, for changing the contribution rates of the differential phase image and the differential absorption image in response to an operation to the operating unit 22. Alternatively, the screen may contain a GUI for changing the contribution rates of both images separately between the bone region and the region other than the bone region.

If an instruction to change the contribution rates is input through the operating unit 22, the control unit 21 calculates a factor corresponding to the contribution rates instructed through the operating unit 22, multiplies the differential absorption image by the factor, and subtracts the differential absorption image multiplied by the factor from the differential phase image, so that the combined image (differential soft-tissue image) based on the changed contribution rates is displayed. The medical doctor manually and freely changes the contribution rates of the differential phase image and the differential absorption image. The medical doctor thus can reduce the factor that the differential absorption image is multiplied by such that the combined image depicts both the bone and the soft tissue for the determination of the position of the soft tissue, or can increase the factor such that the combined image depicts the soft tissue with increased visibility, for example. This control thus can facilitate the diagnosis in soft tissue.

The screen in Step T15 may also contain a button of "slide show" for instructing to stepwise change the contribution rate of the differential absorption image from the minimum to the maximum or vice versa. In this case, if the button of "slide show" is pressed through the operating unit 22, the control unit 21 automatically creates combined images containing the differential absorption images multiplied by the respective factors stepwise changed from the minimum to the maximum or vice versa, and controls the displaying unit 23 to sequentially display the combined images.

The differential soft-tissue image is unfamiliar to most of the medical doctors. In order to facilitate the comparison of the differential soft-tissue image with the absorption image that has been used for the conventional diagnosis, the screen in Step T15 may also contain a combined image of the differential soft-tissue image and the absorption image and a GUI for changing the contribution rates, and may be switched to the display of the combined image based on the relative weighting factors of the differential soft-tissue image and the absorption image that are changed in response to an operation to change the contribution rates through the operating unit 22.

This configuration enables the medical doctor to, for example, stepwise change the ratio of both images such that the combined image changes from the absorption image to the differential soft-tissue image through an operation to the operating unit 22. The medical doctor thus can readily find the correspondence between a portion in the absorption image and the structure (soft tissue) in the differential soft-tissue image. Alternatively, the screen in Step T15 may contain a button for the alternate display, and the displaying unit 23 may alternately display the absorption image and the differential soft-tissue image under an instruction for the alternate display. This configuration enables the medical doctor to compare the signals depicted in the differential soft-tissue image with those in the familiar absorption image. The medical doctor thus can readily find the correspondence between a portion in the absorption image and the structure (soft tissue) in the differential soft-tissue image, and can readily inspect soft tissue.

In the above explanation, the screen in Step T15 contains the GUI for changing the contribution rates of the differential phase image and the differential absorption image to change the factor that the differential absorption image is multiplied by. Alternatively, the screen may contain a GUI for directly changing the factor that the differential absorption image is multiplied by. Alternatively, the displaying unit 23 may display a GUI for changing the threshold for specifying a bone region, alone or together with the GUI for changing the contribution rates or the factor. In this case, the control unit 21 re-creates the differential soft-tissue image based on the threshold changed in response to an operation to the operating unit 22, and controls the displaying unit 23 to display the differential soft-tissue image.

[Third Embodiment]

The third embodiment of the invention will now be described.

According to the third embodiment, the soft-tissue image, which is a combined image of the absorption image and the differential phase image, is created and displayed in the diagnosis of rheumatism in bones and joints.

According to the third embodiment, the combined image table in the storage unit 25 illustrated in FIG. 2 further stores the soft-tissue image, which is the combined image to be created in the diagnosis of rheumatism in bones and joints. The storage unit 25 also stores programs (e.g., a program for executing the process of creating a soft-tissue image illustrated in FIG. 20) for allowing the control unit 21 to execute the operation according to the third embodiment.

The other configurations of the medical imaging system and the respective apparatuses therein are the same as those of the medical imaging system 100 and the respective apparatuses therein according to the first embodiment, and the description thereof is incorporated herein by reference. The operations of the medical imaging system 100 according to the third embodiment will now be explained.

The control unit 21 of the controller 2 executes the image creating and displaying process illustrated in FIG. 3 in response to an operation to the operating unit 22. In Step S5 according to the third embodiment, a soft-tissue image is created by combining the absorption image with a phase image derived from the differential phase image through the process of creating a soft-tissue image (explained below), instead of the creation of the combined image of the absorption image and the differential phase image.

FIG. 20 illustrates the process of creating a soft-tissue image executed by the control unit 21 of the controller 2.

The absorption image and the differential phase image created in Step S4 are acquired (Step S601).

A phase image is then created from the differential phase image (Step S602).

The phase image can be created through the integration of the differential phase image. However, the simple addition from the end pixel in the differential direction would cause the accumulation of noise and the occurrence of linear artifacts. A phase image containing reduced linear artifacts can be created through an optimizing technique, for example, as is disclosed in Known Literature 7 (Non-linear regularized phase retrieval for unidirectional X-ray differential phase contrast radiography; Thuring et al.; OPTICS EXPRESS; Vol. 19; No. 25; 25545-25558; 2011). The optimizing technique involves the minimization of the sum of the absolute difference in the pixel values between two adjacent pixels in the y direction (i.e., the sum of the norms of the differentiation with respect to the y direction) in the plane of the phase image, under the condition that the sum of the squares of the differences (differences between the corresponding pixel values) of an image based on the difference between two adjacent pixels in the x direction (differential direction of the differential phase image) in the phase image from the differential phase image in the plane of the image is smaller than the value defined by the noise.

The absorption image is then multiplied by a factor for adjusting the intensity of signals representing a certain structure (bone, here) in the absorption image to that in the phase image, the certain structure being to be removed from the phase image among anatomical structures common to the phase image and the absorption image (Step S603). In specific, the pixel values of the respective pixels of the absorption image are multiplied by a factor for adjusting the intensity of the signals representing a bone to that in the phase image. The factor may be determined in advance based on the configuration of the apparatus and/or the imaging conditions, or may be calculated before every multiplication. In the latter case, the factor that can achieve the weakest signals representing the same structure (bone) after the subtraction of the absorption image from the phase image, is calculated. For example, the factor may be the ratio (the signals representing the bone in the phase image/the signals representing the bone in the absorption image) of the signals representing the same structure (bone, here), to be subtracted and removed from the phase image, in the phase image to those in the absorption image. For example, in a region of interest, such as the entire region or the region of a bone, the factor may be the ratio of the pixel values (e.g., the ratio of the representative values of the pixel values) in the region of interest between the two images.

Finally, the absorption image multiplied by the factor is then subtracted from the phase image, to create a phase image (soft-tissue image) in which the signals representing a bone are removed or attenuated and which depicts soft tissue with increased visibility (Step S604). In other words, the pixel values of the respective pixels of the absorption image multiplied by the factor are subtracted from the pixel values of the corresponding pixels of the phase image, to create a phase image (soft-tissue image) in which the signals representing the same structure (bone) are removed or attenuated.

Through the process of creating a soft-tissue image, a visible image depicting soft tissue can be created regardless of the overlap of the soft tissue with a bone in the image.

In order to reduce the artifacts caused by the shifts of the lattices, the control unit 21 should preferably correct the artifacts in the acquired differential phase image and create a soft-tissue image with a phase image derived from the corrected differential phase image and the absorption image after the acquisition of the differential phase image in Step S601, as explained in the second embodiment. Alternatively, the unevenness of signals due to a cause other than the subject may be eliminated from the distribution of signals in the phase image and the absorption image, to create a soft-tissue image.

The subtraction of the absorption image from the region that provides sufficient signals from the phase image alone may increase the noise component and lead to degradation of the image quality. To prevent such situation, the factor that the absorption image is multiplied by should thus preferably be reduced in the region other than a bone region in the absorption image. This control can prevent the degradation of the image quality. The process of specifying a bone region is the same as that in the second embodiment, and the explanation thereof is incorporated herein by reference.

After the process of creating a soft-tissue image, the control unit 21 executes the image displaying process in Step S6 in FIG. 3. The image displaying process (FIG. 14) in the diagnosis of rheumatism in bones and joints according to the third embodiment is different from that according to the first or second embodiment. In specific, in Step T15 in FIG. 14, the displaying unit 23 displays the resulting soft-tissue image, which is the combined image of the absorption image and the differential phase image.

The soft-tissue image is created through the removal or attenuation of the signals representing a bone from or in the phase image that depicts signals representing the bone and soft tissue (cartilage), as described above. The soft-tissue image thus allows a medical doctor to view the signals representing the soft tissue, regardless of the overlap of the soft tissue with the bone.

The screen in Step T15 also contains a GUI, such as a button or a slider bar, for changing the contribution rates of the phase image and the absorption image in response to an operation to the operating unit 22. Alternatively, the screen may contain a GUI for changing the contribution rates of both images separately between the bone region and the region other than the bone region.

If an instruction to change the contribution rates is input through the operating unit 22, the control unit 21 calculates the factor corresponding to the instructed contribution rates, multiplies the absorption image by the factor, and subtracts the absorption image multiplied by the factor from the phase image, so that the combined image based on the changed contribution rates is displayed. The medical doctor manually and freely changes the contribution rates of the phase image and the absorption image. The medical doctor thus can reduce the factor that the absorption image is multiplied by such that the combined image depicts both a bone and soft tissue for the determination of the position of the soft tissue, or can increase the factor such that the combined image depicts the soft tissue with increased visibility, for example. This control thus can facilitate the diagnosis in soft tissue.

The screen in Step T15 may also contain a button of "slide show" for instructing to stepwise change the contribution rate of the absorption image from the minimum to the maximum or vice versa. In this case, if the button of "slide show" is pressed through the operating unit 22, the control unit 21 automatically creates combined images containing the absorption images multiplied by the respective factors stepwise changed from the minimum to the maximum or vice versa, and controls the displaying unit 23 to sequentially display the combined images.

The soft-tissue image is unfamiliar to most of the medical doctors. In order to facilitate the comparison of the soft-tissue image with the absorption image that has been used for the conventional diagnosis, the screen in Step T15 may also contain a combined image of the soft-tissue image and the absorption image and a GUI for changing the contribution rates, and may be switched to the display of the combined image based on the relative weighting factors of the soft-tissue image and the absorption image that are changed in response to an operation to change the contribution rates through the operating unit 22.

This configuration enables the medical doctor to, for example, stepwise change the ratio of both images such that the combined image changes from the absorption image to the soft-tissue image through an operation to the operating unit 22. The medical doctor thus can readily find the correspondence between a portion in the absorption image and the structure (soft tissue) in the soft-tissue image. Alternatively, the screen in Step T15 may contain a button for the alternate display, and the displaying unit 23 may alternately display the absorption image and the soft-tissue image under an instruction for the alternate display. This configuration enables the medical doctor to compare the signals depicted in the soft-tissue image with those in the familiar absorption image. The medical doctor thus can readily find the correspondence between a portion in the absorption image and the structure (soft tissue) in the soft-tissue image, and can readily inspect soft tissue.

In the above explanation, the screen in Step T15 contains the GUI for changing the contribution rates of the phase image and the absorption image as the GUI for changing the factor that the absorption image is multiplied by. Alternatively, the screen may contain a GUI for directly changing the factor that the absorption image is multiplied by. Alternatively, the displaying unit 23 may display a GUI for changing the threshold for specifying a bone region, alone or together with the GUI for changing the contribution rates or the factor. In this case, the control unit 21 re-creates the soft-tissue image based on the threshold changed in response to an operation to the operating unit 22, and controls the displaying unit 23 to display the soft-tissue image.

According to the controller 2 of the second or third embodiment, the control unit 21 at least creates a differential phase image and an absorption image in the three reconstructed images (differential phase image, absorption image, and small-angle scattering image) on the basis of image signals representing a subject that are acquired by the X-ray imaging apparatus 1, as described above. The control unit 21 then creates a combined image in which the signals representing a structure common to the differential phase image and the absorption image are removed or attenuated. The removal or attenuation of the signals may be performed by processing the absorption image into a differential absorption image, multiplying the differential absorption image by a factor for adjusting the intensity of the signals representing a structure in the differential absorption image to that in the differential phase image, and subtracting the differential absorption image multiplied by the factor from the differential phase image, in which the structure is common to the differential phase image and the differential absorption image. Alternatively the removal or attenuation may be performed by processing the differential phase image into a phase image, multiplying the absorption image by a factor for adjusting the intensity of signals representing a structure in the absorption image to that in the phase image, and subtracting the absorption image multiplied by the factor from the phase image, in which the structure is common to the phase image and the absorption image.

A visible image depicting a structure hidden behind the structure common to the differential phase image and the absorption image can thus be yielded. For example, a visible image depicting soft tissue, which is hidden behind a bone in the differential phase image, can be yielded.

The factor is a ratio of signals representing the same structure between the two images used for the subtraction. The factor can remove substantially all the signals representing the same structure from the combined image.

The storage unit 25 stores a threshold corresponding to at least one of the absorption image, the differential absorption image, the phase image, the differential phase image, and the small-angle scattering image. The pixel values or the absolute pixel values of a corresponding image is compared with the stored threshold, and the factor for a region having pixel values not exceeding the threshold is reduced to create the combined image. This configuration can prevent the degradation of the image quality caused by an increase in noise.

The displaying unit 23 displays a combined image and a GUI for changing the factor or the threshold, and then displays the combined image re-created based on the factor or the threshold changed in response to an operation to the operating unit 22. This configuration enables a medical doctor to appropriately adjust the factor or the threshold for the diagnosis.

The artifacts in the differential phase image caused by the imaging conditions in the X-ray imaging apparatus 1 are corrected, and the combined image is created with the corrected differential phase image. This configuration can provide stable images suitable for the diagnosis without artifacts.

The embodiments described above are mere examples, and the invention should not be construed to limit the scope of the embodiments.

For example, the specific diagnosis targets are breasts, and bones and joints (rheumatism and a microfracture) in the embodiments, but may also be any other site or disease.

The detailed configurations and the detailed operations of the respective apparatuses constituting the medical imaging system can be appropriately modified within the gist of the invention.

All the disclosure of Japanese Patent Application No. 2012-131596, which was filed on Jun. 11, 2012, including the specification, the claims, the drawings, and the abstract is incorporated herein by reference.

INDUSTRIAL APPLICABILITY

The invention can be applied to a medical imaging system for creating and displaying X-ray images in the medical field.

The invention claimed is:

1. A medical imaging system to create three kinds of reconstructed images of a diagnosis target site in a subject through X-ray imaging of the diagnosis target site with a Talbot or Talbot-Lau imaging apparatus, the three kinds of reconstructed images being an absorption image, a differential phase image, and a small-angle scattering image, the medical imaging system comprising:
   an input unit to receive an input of diagnosis target information for specifying the diagnosis target site, or the diagnosis target site and a disease to be diagnosed in the diagnosis target site; and
   a control unit to create a combined image of two kinds of reconstructed images among the three kinds of reconstructed images on the basis of the diagnosis target information input through the input unit, and to control a displaying unit to display the combined image.

2. The medical imaging system according to claim 1, wherein one of the two kinds of reconstructed images is the absorption image.

3. The medical imaging system according to claim 1, wherein the control unit processes at least one of the two kinds of reconstructed images and then creates the combined image.

4. The medical imaging system according to claim 3, wherein the control unit creates a combined image in which a signal representing a structure common to the differential phase image and the absorption image is removed or attenuated through the following process:
   processing the absorption image into a differential absorption image, multiplying the differential absorption image by a factor for adjusting an intensity of a signal representing a structure in the differential absorption image to an intensity of a signal representing the structure in the differential phase image, the structure being common to the differential phase image and the differential absorption image, and subtracting the differential absorption image multiplied by the factor from the differential phase image, or processing the differential phase image into a phase image, multiplying the absorption image by a factor for adjusting an intensity of a signal representing a structure in the absorption image to an intensity of a signal representing the structure in the phase image, the structure being common to the phase image and the absorption image, and subtracting the absorption image multiplied by the factor from the phase image.

5. The medical imaging system according to claim 1, wherein the control unit creates two or more combined images and controls the displaying unit to simultaneously or alternately display the two or more combined images.

6. The medical imaging system according to claim 1, wherein the control unit controls the displaying unit to simultaneously or alternately display the combined image and at least one of the three kinds of reconstructed images.

7. The medical imaging system according to claim 1, wherein the control unit further creates a combined image of the three kinds of reconstructed images, and controls the displaying unit to simultaneously or alternately display the combined image of the two kinds of reconstructed images and the combined image of the three kinds of reconstructed images.

8. The medical imaging system according to claim 5, wherein the diagnosis target site is breasts.

9. A medical image processing apparatus comprising:
a reconstructed-image creating unit to at least create a differential phase image and an absorption image of three kinds of reconstructed images on the basis of an image signal of a subject acquired with an X-ray imaging apparatus including a Talbot or Talbot-Lau interferometer, the three kinds of reconstructed images being the absorption image, the differential phase image, and a small-angle scattering image; and
a combining unit to create a combined image in which a signal representing a structure common to the differential phase image and the absorption image is removed or attenuated through the following process:
processing the absorption image into a differential absorption image, multiplying the differential absorption image by a factor for adjusting an intensity of a signal representing a structure in the differential absorption image to an intensity of a signal representing the structure in the differential phase image, the structure being common to the differential phase image and the differential absorption image, and subtracting the differential absorption image multiplied by the factor from the differential phase image, or processing the differential phase image into a phase image, multiplying the absorption image by a factor for adjusting an intensity of a signal representing a structure in the absorption image to an intensity of a signal representing the structure in the phase image, the structure being common to the phase image and the absorption image, and subtracting the absorption image multiplied by the factor from the phase image.

10. The medical image processing apparatus according to claim 9, wherein the combining unit calculates a ratio of the signals representing the common structure between the two images used for the subtraction, and uses the ratio as the factor.

11. The medical image processing apparatus according to claim 9, further comprising a storage unit to store a threshold corresponding to at least one of the absorption image, the differential absorption image, the phase image, the differential phase image, and the small-angle scattering image, wherein
the combining unit compares a pixel value or an absolute pixel value of a corresponding one of the images created by the reconstructed-image creating unit with the threshold, reduces the factor for a region having a pixel value not exceeding the threshold, and then creates the combined image.

12. The medical image processing apparatus according to claim 11, further comprising:
a displaying unit to display the combined image; and
an operating unit used for changing the factor and/or the threshold, wherein
the combining unit changes the factor and/or the threshold in response to an operation to the operating unit and then re-creates a combined image, and
the displaying unit displays the combined image re-created based on the changed factor and/or threshold.

13. The medical image processing apparatus according to claim 9, further comprising a correcting unit to correct an artifact in the differential phase image caused by an imaging condition in the X-ray imaging apparatus, wherein
the combining unit creates the combined image with the differential phase image corrected by the correcting unit.

* * * * *